United States Patent
Rajan et al.

(10) Patent No.: US 10,773,045 B2
(45) Date of Patent: Sep. 15, 2020

(54) ANESTHESIA DELIVERY AND VENTILATION SYSTEM

(71) Applicant: Kirura Holding B.V., Huizen (NL)

(72) Inventors: Govinda Nallappa Rajan, Huizen (NL); Diederik Antonius Maria Paulus Johannes Gommers, Wijngaarden (NL)

(73) Assignee: Kirura Holding B.V., Huizen (NL)

( * ) Notice: Subject to any disclaimer, the term of this patent is extended or adjusted under 35 U.S.C. 154(b) by 959 days.

(21) Appl. No.: 15/281,121

(22) Filed: Sep. 30, 2016

(65) Prior Publication Data

US 2018/0093063 A1    Apr. 5, 2018

(51) Int. Cl.
*A61M 16/10* (2006.01)
*A61M 16/12* (2006.01)
(Continued)

(52) U.S. Cl.
CPC .... *A61M 16/0891* (2014.02); *A61M 16/0045* (2013.01); *A61M 16/0066* (2013.01); *A61M 16/0078* (2013.01); *A61M 16/0081* (2014.02); *A61M 16/01* (2013.01); *A61M 16/0816* (2013.01); *A61M 16/0875* (2013.01); *A61M 16/104* (2013.01); *A61M 16/1005* (2014.02); *A61M 16/12* (2013.01);
(Continued)

(58) Field of Classification Search
CPC .. A61M 16/00; A61M 16/0051; A61M 16/01; A61M 16/06; A61M 16/08; A61M 16/0891; A61M 16/0883; A61M 16/10; A61M 16/12; A61M 16/18; A61M 16/22; A61M 2016/1025; A61M 2016/0039; A61M 2205/3368; A61M 2205/3334; B63C 11/00; B63C 11/02; B63C 11/34–36; A62B 7/00; A62B 7/02; A62B 7/04; A62B 7/08
See application file for complete search history.

(56) References Cited

U.S. PATENT DOCUMENTS 3,823,738 A * 7/1974 Weninger .............. A61M 16/20
                                                                137/613
4,340,044 A * 7/1982 Levy ................... A61M 16/024
                                                              128/204.21
(Continued)

*Primary Examiner* — Samchuan C Yao
*Assistant Examiner* — Ned T Heffner
(74) *Attorney, Agent, or Firm* — Ashok Tankha

(57) ABSTRACT

An anesthesia delivery and ventilation system (ADVS) includes an expiratory section, a circulation flow system (CFS), an inspiratory section, a ventilation drive system (VDS), and an anesthesia delivery system (ADS). The expiratory section receives gases from a patient and the inspiratory section and fresh gases from a fresh gas supply system. An elastic mixing reservoir receives and mixes the gases circulated by the CFS with residual gases via a connector element. The inspiratory section connects to the expiratory section at one end and to a patient connector tube at the other end. The ADS infuses an anesthetic agent into the mixed gases in the inspiratory section. The VDS delivers the mixed gases with the anesthetic agent to the patient. The VDS and the CFS are controlled and operate independently of each other to provide positive end-expiratory pressure control and ventilation control to the patient without use of a proportional valve.

12 Claims, 9 Drawing Sheets

(51) Int. Cl.
*A61M 16/08* (2006.01)
*A61M 16/01* (2006.01)
*A61M 16/00* (2006.01)
*A61M 16/18* (2006.01)
*A61M 16/22* (2006.01)
*A61M 16/20* (2006.01)
*A61M 16/06* (2006.01)

(52) U.S. Cl.
CPC ....... *A61M 16/0069* (2014.02); *A61M 16/022* (2017.08); *A61M 16/024* (2017.08); *A61M 16/06* (2013.01); *A61M 16/08* (2013.01); *A61M 16/18* (2013.01); *A61M 16/209* (2014.02); *A61M 16/22* (2013.01); *A61M 2016/0027* (2013.01); *A61M 2016/0036* (2013.01); *A61M 2016/0039* (2013.01); *A61M 2016/0042* (2013.01); *A61M 2016/1035* (2013.01); *A61M 2205/3334* (2013.01); *A61M 2205/3368* (2013.01)

(56) References Cited

U.S. PATENT DOCUMENTS

| | | | |
|---|---|---|---|
| 4,657,710 A * | 4/1987 | Smith | A61M 16/18 261/46 |
| 5,339,807 A | 8/1994 | Carter | |
| 5,509,406 A * | 4/1996 | Kock | A61M 16/104 128/200.24 |
| 6,131,571 A | 10/2000 | Lampotang et al. | |
| 9,238,115 B2 | 1/2016 | Homuth et al. | |
| 2008/0283059 A1 | 11/2008 | Siegel et al. | |
| 2011/0061650 A1 | 3/2011 | Heesch | |
| 2013/0255687 A1 | 10/2013 | Rahlf et al. | |

* cited by examiner

ANESTHESIA DELIVERY AND VENTILATION SYSTEM

BACKGROUND

An anesthesia circulating loop is used for delivering gases comprising oxygen and other gases optionally infused with an inhalational anesthetic agent to a patient under positive end-expiratory pressure and for providing ventilation control to the patient. Positive end-expiratory pressure is the pressure in the lungs of a patient, clinically referred to as "alveolar pressure", at the end of expiration. As used herein, the term "ventilation" refers to a process of providing mechanical assistance to a patient for breathing. The anesthesia circulating loop comprises an expiratory section and an inspiratory section. The anesthesia circulating loop allows breathing gases to be forced into the patient to preclude apnea, which is a major effect of anesthesia. As used herein, "breathing gases" refer to gases inhaled by the patient from the anesthesia circulating loop and gases exhaled by the patient into the anesthesia circulating loop during breathing. Also, as used herein, "inspiratory section gases" refer to gases transported along the inspiratory section of the anesthesia circulating loop, which are inhaled or inspired by a patient from the inspiratory section of the anesthesia circulating loop and gases bypassing inhalation and transported directly into the expiratory section of the anesthesia circulating loop. Also, as used herein, "expiratory section gases" refer to gases that are exhaled or expired by the patient into the expiratory section of the anesthesia circulating loop and gases bypassing inhalation and transported directly into the expiratory section from the inspiratory section which are not exhaled by the patient, both of which are transported along the expiratory section of the anesthesia circulating loop.

Conventional anesthesia delivery systems are typically configured as bag-in-box systems, where a circulation blower provides a continuous flow of gases and a ventilation drive provides ventilation into a box, which moves a bag. The ventilation drive typically includes another blower or pressurized air. A conventional bag-in-box system, also referred to as a bellows system, with a single in-line blower is a complex mechanical system and introduces additional cost and disturbance in ventilation patterns. Moreover, conventional bag-in-box systems have a single connection for inspiratory section gases and expiratory section gases that preclude complete mixing of the inspiratory section gases and the expiratory section gases, especially in low breathing volumes. Other conventional anesthesia delivery systems use a cylinder-piston system similar to the bag-in-box system. In addition to the costs involved and disturbances in ventilation patterns, conventional cylinder-piston type anesthesia delivery systems are more prone to leakage of gases and pose a high risk of occurrence of a negative end-expiratory pressure, which is a subatmospheric pressure that develops at a patient's airway at the end of expiration.

In other conventional anesthesia delivery systems, a combination of a ventilation blower and a ventilation valve provides ventilation to a patient. In these systems, a positive end-expiratory pressure is maintained in a circulating flow of gases by a complex feedback control system based on a set of flow sensors and control of the ventilation valve and the ventilation blower, which results in oscillations and a substantially slow reaction to remove the oscillations. Moreover, in conventional systems, a substantially large volume of gases retained in a conventional reservoir is bypassed by the circulation flow. When ventilation starts, a large offset occurs due to a previously unmixed volume of gases.

A positive end-expiratory pressure of about 2 cm water ($H_2O$) to about 10 cm $H_2O$ is required to be maintained in the lungs of a patient to keep the lungs open and to prevent the lungs from collapsing during or at the end of expiration, or to assist with lung inflation, that is, alveolar inflation, during the ventilation of the patient. The positive end-expiratory pressure helps to keep the lungs, that is, the alveoli, open and reduces pulmonary edema, that is, ingress of liquid from the capillaries into the alveoli. The pressure inside the lungs at the end of expiration is typically about 0 cm $H_2O$, that is, atmospheric pressure. A conventional anesthesia delivery system comprises a circulating loop with a flow proportional valve in the expiratory section of the circulating loop for restricting the flow of breathing gases, thereby creating a back pressure upstream of the flow proportional valve. The back pressure results in the creation of a positive end-expiratory pressure in the lungs of the patient by restricting the flow of breathing gases upstream of the flow proportional valve. The positive end-expiratory pressure is typically preset at about 2 cm $H_2O$ to about 10 cm $H_2O$. In the anesthesia art, a flow proportional valve that functions to create a positive end-expiratory pressure in an anesthesia circulating loop is referred to as a positive end-expiratory pressure valve. A positive end-expiratory pressure valve is used in a conventional anesthesia circulating loop to maintain a pressure of about 2 cm $H_2O$ to about 4 cm $H_2O$ above atmospheric pressure within the patient's lungs. The positive end-expiratory pressure valve is typically positioned on an expiratory section of the anesthesia circulating loop with the position of the positive end-expiratory pressure valve selected by a manufacturer of the anesthesia circulating loop. In a conventional system, an adjustable spring located within the positive end-expiratory pressure valve is used for regulating the positive end-expiratory pressure at about 2 cm $H_2O$ to about 10 cm $H_2O$ in the patient's lungs at the end of expiration. In another conventional system, the 2 cm $H_2O$ to 10 cm $H_2O$ positive end-expiratory pressure required to be maintained in the lungs is obtained by adjusting a knob extending out of a clear dome of the positive end-expiratory pressure valve. In another conventional system, the positive end-expiratory pressure is regulated by changing the tension on a spring located inside a device on the expiratory section of the anesthesia circulating loop. In another conventional system, a heat and moisture exchanger type insert fitted between an expiratory limb and an expiratory limb port function as a positive end-expiratory pressure valve.

Some conventional anesthesia delivery and ventilation systems have a ball bearing in the positive end-expiratory pressure valve that provides gravity-induced resistance to exhalation. This positive end-expiratory pressure valve has to be oriented perpendicular to a ground surface to work properly. The positive end-expiratory pressure valve is not adjustable. If a user wants to go from 2 cm $H_2O$ to 10 cm $H_2O$, the user is required to use a different valve with a heavier ball bearing. If the positive end-expiratory pressure valve is inadvertently installed upside down, the anesthesia circulating loop will be completely blocked. Moreover, resistance to exhalation stays the same when switching from a ventilator mode to a bag mode. Other conventional anesthesia machines have positive end-expiratory pressure valves that are electrically controlled to deliver the amount of positive end-expiratory pressure that is dialed into ventilator controls. With electrically controlled positive end-expiratory pressure valves, the positive end-expiratory pressure returns to zero when the anesthesia machine is switched from the ventilator mode to the bag mode.

To obtain the desired 2 cm $H_2O$ to 10 cm $H_2O$ positive end-expiratory pressure, at the start of an expiration phase, a command pressure maintained by an exhalation valve is lowered either abruptly or gradually from a desired inspiration pressure to the desired positive end-expiratory pressure. The patient exhales in the expiration phase. In a conventional anesthesia delivery system, the system pressure undergoes a steep drop initially, and oscillates about the desired positive end-expiratory pressure at a typical frequency of the anesthesia delivery system until equilibrium is reached. The frequency and amplitude of the oscillation depends, for example, on compressibility and volume of a respiratory gas, tolerances of components of the ventilation system, and the patient's health condition. The amplitude and duration of the oscillation at the beginning of the expiration phase can be substantial.

Some conventional systems use only a single in-line blower to provide both a continuous flow of gases and ventilation. In other conventional systems, an inline blower and a ventilation blower are used to provide both a continuous flow of gases and ventilation. In both these systems, a proportional valve, for example, a positive end-expiratory pressure valve is used for controlling the continuous flow of gases and ventilation patterns at the same time. There are several problems associated with the use of a proportional valve, for example, a positive end-expiratory pressure valve, to create a positive end-expiratory pressure in an anesthesia circulating loop. A positive end-expiratory pressure valve installed in the expiratory section of the anesthesia circulating loop increases the resistance to flow of the gases exhaled by the patient, and increases the breathing effort of the patient especially in low ventilation volumes. Moreover, the positive end-expiratory pressure valve increases the complexity of a control algorithm for simultaneously controlling the continuous flow of gases and ventilation patterns. For example, when there is no breath pattern needed, the positive end-expiratory pressure valve is kept completely open and the in-line blower is run at the lowest pressure and flow rate required for the continuous flow of gases. During inspiration and expiration, both the positive end-expiratory pressure valve and power to the single in-line blower and/or the power to the in-line blower and the ventilation blower must be controlled simultaneously and continuously to produce the required continuous flow of gases and inspiration pattern. The simultaneous and continuous control of the positive end-expiratory pressure valve and the power to the in-line blower and the ventilation blower increases the risk of an interruption or a lower than an optimal volume of the continuous flow of breathing gases. Furthermore, the use of a positive end-expiratory pressure valve increases the risk of a delay in the switching time between breath phases, for example, from expiration to inspiration. For example, with the use of a positive end-expiratory pressure valve, the inspiration cycle is maintained by closing the positive end-expiratory pressure valve, either completely or partially. To switch from inspiration to expiration, the positive end-expiratory pressure valve is opened to the level where the required positive end-expiratory pressure is maintained in the anesthesia circulating loop. During assisted ventilation, where the breathing effort of the patient is used as a trigger to start an inspiration or expiration, the positive end-expiratory pressure valve is controlled accordingly, which introduces a corresponding delay in opening or closing of the positive end-expiratory pressure valve, which in turn, can increase the breathing effort of the patient. The delay in the operation of the positive end-expiratory pressure valve also increases the risk of pressure oscillations of breathing gases in the positive end-expiratory pressure value during expiration. Furthermore, it is difficult to accurately control the positive end-expiratory pressure by a positive end-expiratory pressure valve at a narrow preset range of, for example, about 2 cm $H_2O$ to 10 cm $H_2O$ for an extended period of time, due in part to the time required to adjust the positive end-expiratory pressure valve in response to changing physiological and breathing conditions of a patient.

Interconnections between sections, for example, the expiratory section, the inspiratory section, etc., of the anesthesia circulating loop are based on tube connections where one tube is inserted into another tube. The interconnections are generally airtight and can be easily removed and reconnected. However, in conventional systems where a turbine is used for a blower, for example, the circulation blower, the housing of the turbine has two tubes on both sides that can be attached using tubes to the rest of the circuit. The housing of the turbine is made up of two halves with the turbine in between the two halves. To sterilize the turbine, the halves are dismantled and the turbine is removed. After sterilization, the turbine is placed between the halves of the housing and is clamped such that the turbine can rotate freely while joints between the turbine and the halves of the housing are airtight. The type of joint used between the turbine and the halves of the housing is prone to leakage. As used herein, "leakage" refers to leakage of gases from the anesthesia circulating loop at points of interconnection between different sections of the anesthesia circulating loop and at points where a turbine of a blower is mounted in the anesthesia circulating loop for in-line blowers if any. There is a need for preventing leakage of gases from the anesthesia circulating loop.

Hence, there is a long felt need for a method and an anesthesia delivery and ventilation system for delivering inspiratory section gases optionally infused with an inhalational anesthetic agent to a patient and for controlling positive end-expiratory pressure and ventilation without the use of a proportional valve. Moreover, there is a need for an anesthesia delivery and ventilation system that ensures uniform mixing of expiratory section gases and fresh gases that constitute the inspiratory section gases and that allows the inspiratory section gases in the inspiratory section to reach a required composition. Furthermore, there is a need for an anesthesia delivery and ventilation system where continuous circulation of the expiratory section gases and flow of the inspiratory section gases are controlled independently. Furthermore, there is a need for an anesthesia delivery and ventilation system that is less prone to leakage of gases from the anesthesia delivery and ventilation system compared to conventional anesthesia delivery systems.

SUMMARY OF THE INVENTION

This summary is provided to introduce a selection of concepts in a simplified form that are further disclosed in the detailed description of the invention. This summary is not intended to determine the scope of the claimed subject matter.

The anesthesia delivery and ventilation system and the method disclosed herein address the above mentioned needs for delivering inspiratory section gases optionally infused with an inhalational anesthetic agent to a patient and for controlling positive end-expiratory pressure and ventilation without the use of a proportional valve. The anesthesia delivery and ventilation system disclosed herein comprises a circulating loop comprising at least two in-line blowers, namely, a circulation blower and a ventilation blower, wherein the circulation blower and the ventilation blower are controlled independently of each other for providing a continuous flow of expiratory section gases and inspiratory section gases in the circulating loop and for controlling positive end-expiratory pressure and ventilation patterns of the inspiratory section gases and anesthesia vapor infused in the inspiratory section gases for administration to a patient without the use of a proportional valve for positive end-expiratory pressure control and ventilation control. In the anesthesia delivery and ventilation system disclosed herein, continuous circulation of the expiratory section gases and flow of the inspiratory section gases are controlled independently. The anesthesia delivery and ventilation system disclosed herein ensures uniform mixing of expiratory section gases, fresh gases, and residual gases retained in a reservoir, and allows the resulting inspiratory section gases in the circulating loop to reach a required composition. In an embodiment, the anesthesia delivery and ventilation system disclosed herein replaces an in-line blower used in conventional anesthesia delivery systems with an elastic mixing reservoir that makes the anesthesia delivery and ventilation system less prone to leakage of gases from the anesthesia delivery and ventilation system compared to conventional anesthesia delivery systems.

The anesthesia delivery and ventilation system disclosed herein comprises an expiratory section, a circulation flow system, an inspiratory section, a ventilation drive system, and an anesthesia delivery system. The expiratory section comprises a first end and a second end. The first end of the expiratory section is operably connected to a patient connector tube for receiving expiratory section gases, that is, gases exhaled by a patient via the patient connector tube and gases bypassing inhalation and transported directly into the expiratory section from the inspiratory section. The second end of the expiratory section is operably connected proximal to a fresh gas supply system for receiving fresh gases from the fresh gas supply system for increasing the concentration of the received gases to a gas component level required to be maintained in the inspiratory section of the circulating loop. The circulation flow system is operably positioned at a predetermined location in the expiratory section for circulating the received gases. The circulation flow system is controlled by a feedback control loop based on flow rate, temperature, and pressure of the fresh gases, the received gases in the expiratory section, and gases in the inspiratory section provided by flow rate, temperature and pressure sensors. The flow rate, temperature and pressure sensors are positioned at predetermined locations within the anesthesia delivery and ventilation system. The fresh gases from the fresh gas supply system are mixed with the circulating gases proximal to the second end of the expiratory section.

The inspiratory section is in fluid communication with the circulation flow system and the fresh gas supply system at the second end of the expiratory section. The inspiratory section comprises a first end and a second end. The first end of the inspiratory section is proximal to and in fluid communication with the second end of the expiratory section. The second end of the inspiratory section is operably connected to the patient connector tube. The inspiratory section receives fresh gases mixed with the circulating gases from the expiratory section to form mixed gases. The mixed gases are optionally infused with an inhalational anesthetic agent to form inspiratory section gases. In a ventilation mode of operation, the ventilation drive system is operably positioned at a predetermined location in the inspiratory section for delivering the inspiratory section gases, that is, the mixed gases comprising oxygen and other gases optionally infused with the inhalational anesthetic agent to the patient and for providing ventilation control to the patient when the lungs of the patient are ventilated. In the ventilation mode of operation, the inspiratory section gases are transported through the inspiratory section for ventilating the patient's lungs. The ventilation drive system and the circulation flow system are configured to provide flow control of the inspiratory section gases in the inspiratory section to the patient. The ventilation drive system and the circulation flow system are controlled by a computer system and operate independently of each other to provide control of positive end-expiratory pressure of about 2 cm $H_2O$ to about 10 cm $H_2O$ and ventilation control to the patient without the use of a proportional valve in the circulating loop of the anesthesia delivery and ventilation system.

The anesthesia delivery system comprises an anesthesia delivery tube operably connected to and in fluid communication with the inspiratory section of the circulating loop. The anesthesia delivery tube is positioned between the first end of the inspiratory section and the second end of the inspiratory section. The anesthesia delivery tube infuses and vaporizes a predetermined amount of an inhalational anesthetic agent into the mixed gases in the inspiratory section. The ventilation drive system delivers a portion of the inspiratory section gases, that is, the mixed gases with the inhalational anesthetic agent, to the patient connector tube for inhalation by the patient and a remaining portion of the inspiratory section gases to the expiratory section.

In an embodiment, the anesthesia delivery and ventilation system further comprises at least one elastic mixing reservoir in fluid communication with the circulation flow system and the fresh gas supply system via a connector element for receiving and mixing the circulating gases from the circulation flow system and the fresh gases from the fresh gas supply system with residual gases contained in the elastic mixing reservoir. The connector element comprising a stopper with an inlet tube and an outlet tube is positioned on an upper end of the elastic mixing reservoir for allowing the expiratory section gases and the fresh gases to be fed into the elastic mixing reservoir, and for allowing the expiratory section gases, the fresh gases, and the residual gases in the elastic mixing reservoir to be mixed and discharged into the inspiratory section of the anesthesia delivery and ventilation system.

In one or more embodiments, related systems comprise circuitry and/or programming for effecting the methods disclosed herein. The circuitry and/or programming can be any combination of hardware, software, and/or firmware configured to effect the methods disclosed herein depending upon the design choices of a system designer. Also, various structural elements can be employed depending on the design choices of the system designer.

BRIEF DESCRIPTION OF THE DRAWINGS

The foregoing summary, as well as the following detailed description of the invention, is better understood when read in conjunction with the appended drawings. For illustrating the invention, exemplary constructions of the invention are shown in the drawings. However, the invention is not limited to the specific methods, structures, and components disclosed herein. The description of a method step or a structure or a component referenced by a numeral in a drawing is applicable to the description of that method step or structure or component shown by that same numeral in any subsequent drawing herein.

DETAILED DESCRIPTION OF THE INVENTION

Figure 1:
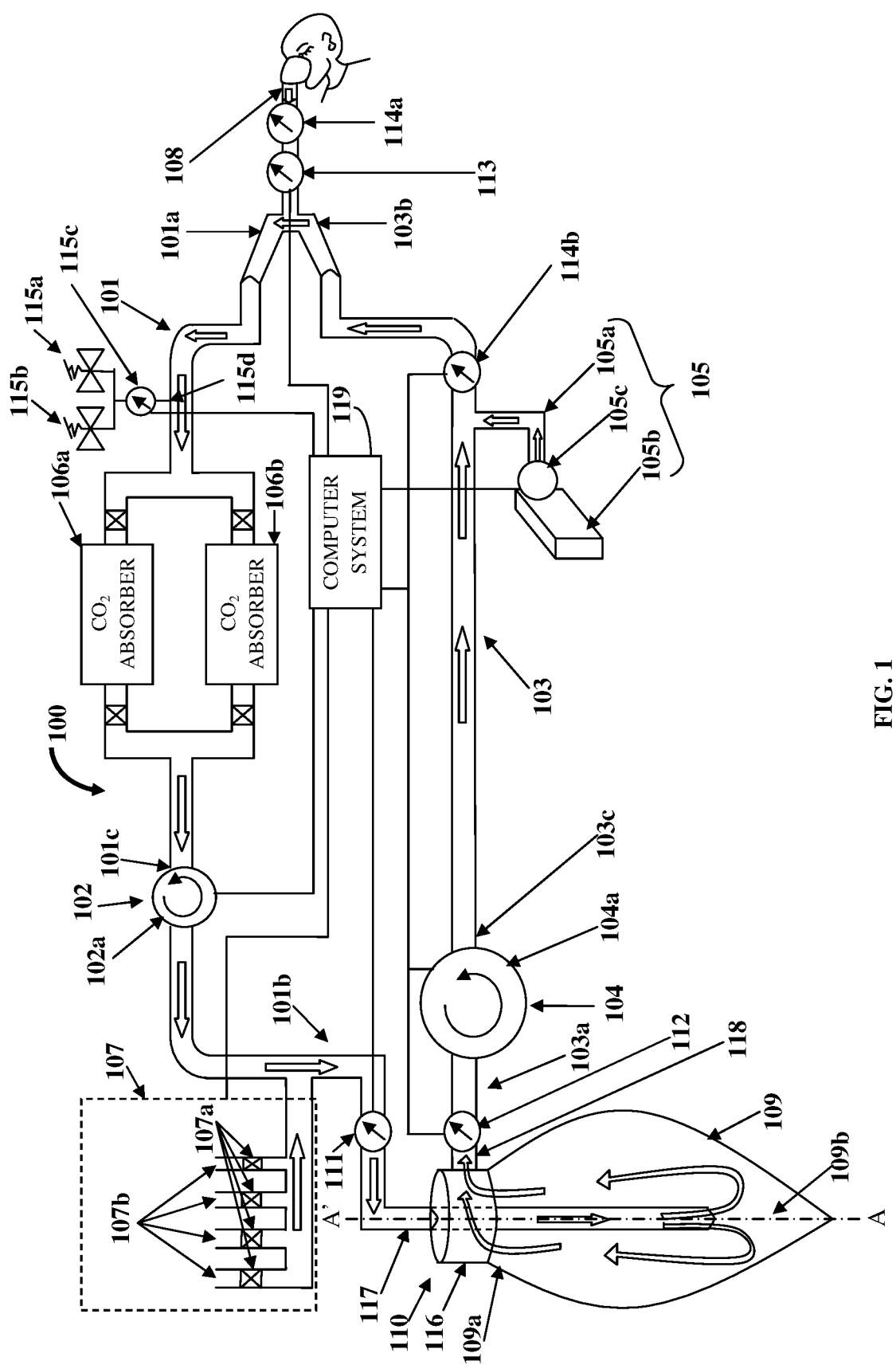
FIG. 1 illustrates an anesthesia delivery and ventilation system for delivering an inhalational anesthetic agent infused in air and other gases to a patient via a circulating loop for controlling flow and concentration of inspiratory section gases for administration to the patient and for recirculating expiratory section gases.

FIG. 1 illustrates an anesthesia delivery and ventilation system 100 for delivering an inhalational anesthetic agent infused in air and other gases to a patient via a circulating loop for controlling flow and concentration of inspiratory section gases for administration to the patient, and for recirculating expiratory section gases. As used herein, "circulating loop" refers to a continuous loop in the anesthesia delivery and ventilation system 100 comprising an expiratory section 101 extending from a first end 101a to a second end 101b and an inspiratory section 103 extending from a first end 103a to a second end 103b, in which the expiratory section gases and the inspiratory section gases respectively, are circulated. Also, as used herein, "inspiratory section gases" refer to gases transported along the inspiratory section 103 of the circulating loop that extends from the first end 103a of the inspiratory section 103 to the second end 103b of the inspiratory section 103. Inspiratory section gases comprise a mixture of expiratory section gases substantially free of carbon dioxide and fresh gases supplied by a fresh gas supply system 107 that are transported in the inspiratory section 103 for inhalation by the patient. In an embodiment, inspiratory section gases comprise a mixture of expiratory section gases substantially free of carbon dioxide and fresh gases supplied by the fresh gas supply system 107, which are mixed and thereafter infused with an inhalational anesthetic agent. Also, as used herein, "expiratory section gases" refer to gases exhaled by the patient into the expiratory section 101 of the circulating loop and gases bypassing inhalation and transported directly into the expiratory section 101 from the inspiratory section 103 which are not exhaled by the patient, both of which are transported along the expiratory section 101 of the circulating loop that extends from the first end 101a of the expiratory section 101 to the second end 101b of the expiratory section 101.

Also, as used herein, "expiratory section" refers to an assembly of components, for example, one or more carbon dioxide ($CO_2$) absorbers 106a and 106b, a circulation flow system 102 comprising a circulation blower 102a, a fresh gas supply system 107 comprising one or more fresh gas supply tubes 107b, etc., that extends from the first end 101a of the expiratory section 101 to the second end 101b of the expiratory section 101 through which the expiratory section gases flow. Also, as used herein, "expiration" refers to a discharge of gases exhaled by a patient from the patient's lungs through the patient's nose, the patient's mouth, or an endotracheal tube. The expiratory section 101 not only receives the exhaled gases from the patient but also the gases that are not inhaled by the patient and that are transported directly from the inspiratory section 103 to the expiratory section 101. The expiratory section gases provide a portion of the gases that are circulated in the circulating loop, but are not used for inhalation. Also, as used herein, "inspiratory section" refers to an assembly of components, for example, a ventilation drive system 104 comprising a ventilation blower 104a, an anesthesia delivery system 105, etc., for transporting the inspiratory section gases from the first end 103a of the inspiratory section 103 to the patient's airway comprising the patient's nose, the patient's mouth, and/or the endotracheal tube along with the infused inhalational anesthetic agent for inhalation by the patient at the second end 103b of the inspiratory section 103. Also, as used herein, "inspiration" refers to a process of inhaling the inspiratory section gases by a patient with or without an inhalational anesthetic agent through the patient's nose, the patient's mouth, or the endotracheal tube. The inspiratory section 103 not only provides the gases inhaled by the patient but also provides a continuous flow of gases from the inspiratory section 103 to the expiratory section 101 directly.

In general, there is always a flow of gases, referred herein as a "circulation flow", in the circulating loop, both in the inspiratory section 103 and the expiratory section 101 at all times, that is, during inspiration, expiration, and when there is no breathing by the patient. During inspiration, the inspiratory section gases provide a flow of gases to the patient for inhalation and a flow of gases directly from the inspiratory section 103 to the expiratory section 101. The expiratory section 101 has a flow of gases that comes directly from the inspiratory section 103. During inspiration, the circulation flow is the flow of gases that is not inhaled and that flows from the inspiratory section 103 to the expiratory section 101 and then back to the inspiratory section 103 with injected fresh gases if required. During expiration, the inspiratory section gases provide a flow of gases directly to the expiratory section 101. The expiratory section 101 has a flow of gases that comes directly from the inspiratory section 103 and the flow of gases from exhalation by the patient. During expiration, the circulation flow is the flow of gases from the inspiratory section 103 to the expiratory section 101 and then back to the inspiratory section 103 with the exhaled gases and injected fresh gases if required. When there is no breathing, the inspiratory section gases provide a flow of gases to the expiratory section 101, while the expiratory section gases comprise the flow of gases from the inspiratory section 103. When there is no breathing, the circulation flow is the flow of gases from the inspiratory section 103 to the expiratory section 101 and then back to the inspiratory section 103 mixed with injected fresh gases if required.

Also, as used herein, "ventilation" refers to a process of mechanically assisting a patient to breathe, that is, by mechanically transporting inspiratory section gases into and expiratory section gases out of the lungs of the patient using the anesthesia delivery and ventilation system 100. In an embodiment, "ventilation" also refers to providing inspiratory section gases using the anesthesia delivery and ventilation system 100 to a patient who is physically unable to breathe, or who is breathing insufficiently.

The inner diameter of tubes that form the anesthesia delivery and ventilation system 100 comprising the expiratory section 101 extending from the first end 101a to the second end 101b and the inspiratory section 103 extending from the first end 103a to the second end 103b is, for example, about 22 millimeters (mm). The anesthesia delivery and ventilation system 100 is configured, for example, as a closed loop system. In an embodiment, the anesthesia delivery and ventilation system 100 is configured as a semi-closed loop system. In another embodiment, the anesthesia delivery and ventilation system 100 is configured as an open loop system. As exemplarily illustrated in FIG. 1, the first end 101a of the expiratory section 101 is operably connected to a patient connector tube 108. The patient connector tube 108 is connected to the patient's airway, via, for example, an endotracheal tube, a mask, etc., to receive gases exhaled by the patient. The first end 101a of the expiratory section 101 operably connected to the patient connector tube 108 receives gases exhaled by the patient via the patient connector tube 108 and gases bypassing inhalation and transported directly into the expiratory section 101 from the inspiratory section 103. During breathing, the patient's body inspires oxygen ($O_2$)-rich gases, and exhales gases with a higher carbon dioxide ($CO_2$) content than the carbon dioxide content in the inspiratory section gases. The gases comprising carbon dioxide are exhaled by the patient into the expiratory section 101 via the patient connector tube 108 and constitute the expiratory section gases. In an embodiment, one or more carbon dioxide absorbers 106a and 106b are positioned between the first end 101a of the expiratory section 101 and the second end 101b of the expiratory section 101 for reducing carbon dioxide from the expiratory section gases. In an embodiment, the carbon dioxide absorbers 106a and 106b are positioned in a parallel configuration as exemplarily illustrated in FIG. 1. When the inspiratory section gases comprise air, the expiratory section gases, before passing through the carbon dioxide absorbers 106a and 106b, comprise, for example, about 78.04% nitrogen, about 13.6% to about 16% oxygen, about 4% to about 5.3% carbon dioxide, water vapor, and small traces of other gases. The carbon dioxide concentration of the expiratory section gases is reduced, for example, from about 4% to about 5% to less than about 0.5% by passing the expiratory section gases through the carbon dioxide absorbers 106a and 106b.

The circulation blower 102a of the circulation flow system 102 is operably positioned in-line at a predetermined location 101c in the expiratory section 101 for continuously circulating the expiratory section gases substantially free of carbon dioxide from the first end 101a of the expiratory section 101 towards the second end 101b of the expiratory section 101. The circulation blower 102a circulates the expiratory section gases and the inspiratory section gases in the circulating loop in the expiratory section 101 and the inspiratory section 103 respectively. An example of the capacity of the circulation blower 102a is about 60 liters per minute. The circulation flow system 102 is controlled by a feedback control loop based on flow rate, temperature, and pressure of the fresh gases provided by a first flow rate, temperature and pressure sensor 111, flow rate, temperature, and pressure of the expiratory section gases in the expiratory section provided by a second flow rate, temperature and pressure sensor 112 and a third flow rate, temperature and pressure sensor 113, and flow rate, temperature, and pressure of the inspiratory section gases in the inspiratory section 103 provided by the third flow rate, temperature and pressure sensor 113 and a fourth flow rate, temperature and pressure sensor 115c. The first flow rate, temperature and pressure sensor 111, the second flow rate, temperature and pressure sensor 112, the third flow rate, temperature and pressure sensor 113, and the fourth flow rate, temperature and pressure sensor 115c are positioned at predetermined locations within the anesthesia delivery and ventilation system 100 as exemplarily illustrated in FIG. 1.

In an embodiment, a breathing gas concentration sensor 114b is mounted on the inspiratory section 103 for monitoring and measuring a concentration of each gas in the mixture of the fresh gases, the expiratory section gases, the inspiratory section gases, and the inhalational anesthetic agent in the inspiratory section 103. Also, a breathing gas concentration sensor 114a positioned at the patient connector tube 108 measures the concentration of the inspiratory section gases and the expiratory section gases at the patient connector tube 108. In an embodiment, the anesthesia delivery and ventilation system 100 comprises a computer system 119 in electrical communication with the breathing gas concentration sensors 114a and 114b, the flow rate, temperature and pressure sensors 111, 112, 113, and 115c, the circulation flow system 102, the ventilation drive system 104, and gas inlet valves 107a in the fresh gas supply system 107, the anesthesia delivery system 105, the inspiratory section 103, and the expiratory section 101 for controlling the circulation flow system 102 and the ventilation drive system 104 to provide a positive end-expiratory pressure of about 2 cm water ($H_2O$) to 10 cm $H_2O$ and ventilation control to the patient without the use of a proportional valve in the circulating loop of the anesthesia delivery and ventilation system 100.

The second end 101b of the expiratory section 101 is operably connected proximal to one or more fresh gas supply tubes 107b of the fresh gas supply system 107 for receiving fresh gases, for example, oxygen, xenon, air, etc., on an as required basis. The fresh gases are mixed with the expiratory section gases for increasing the concentration of the gases circulating from the second end 101b of the expiratory section 101 towards the first end 103a of the inspiratory section 103 to a gas component level required to be maintained in the inspiratory section 103. As used herein, "gas component level" refers to a concentration level of each individual gas, for example, oxygen ($O_2$), carbon dioxide ($CO_2$), xenon, etc., in the expiratory section gases. The fresh gases from the fresh gas supply system 107 mix with the circulating expiratory section gases proximal to the second end 101b of the expiratory section 101. Consider an example where the settings of the anesthesia delivery and ventilation system 100 are set to change the gas concentrations of the gases in the inspiratory section 103 from air to a higher oxygen concentration, for example, about 50% oxygen. A gas inlet valve for oxygen from the gas inlet valves 107a in the fresh gas supply system 107 with a capacity of, for example, about 12 liters per minute, is opened either continuously or in timed open and closed pulses by a feedback control loop in the computer system 119 to increase the oxygen concentration to about 50% as measured by the breathing gas concentration sensor 114b.

As used herein, the operation of a blower comprises speed in rotations per minute (rpm) of the blower and the corresponding flow rate of the blower, etc. In an embodiment, the operation of the ventilation blower 104a of the ventilation drive system 104 in the inspiratory section 103 is controlled by the computer system 119 based on a first feedback control loop from the third flow rate, temperature and pressure sensor 113 to the computer system 119. The operation of the circulation blower 102a in the circulation flow system 102 is controlled by the computer system 119 based on a second feedback control loop from a combination of the first flow rate, temperature and pressure sensor 111, the second flow rate, temperature and pressure sensor 112, the third flow rate, temperature and pressure sensor 113, and the fourth flow rate, temperature and pressure sensor 115c to the computer system 119. The second feedback control loop that controls the operation of the circulation blower 102a is separate and distinct from the first feedback control loop that controls the operation of the ventilation blower 104a. The ventilation drive system 104 and the circulation flow system 102 are controlled by the computer system 119 independently of each other and operate independently of each other to provide positive end-expiratory pressure control and ventilation control to the patient at the patient connector tube 108 without the use of a proportional valve in the circulating loop of the anesthesia delivery and ventilation system 100.

In an embodiment, the feedback control loop in the computer system 119 automatically compensates for a pressure drop from the first end 101a of the expiratory section 101 to the second end 101b of the expiratory section 101 by increasing or decreasing the flow rate and discharge pressure of the ventilation blower 104a based on the pressure measured by the third flow rate, temperature and pressure sensor 113. Consider an example where the pressure at the patient connector tube 108 in the anesthesia delivery and ventilation system 100 is required to be maintained at a preset pressure of about 10 cm $H_2O$ to about 15 cm $H_2O$ during inspiration. In an embodiment, at the start of inspiration, the feedback control loop from the third flow rate, temperature and pressure sensor 113 to the computer system 119 increases or decreases the volumetric flow rate and discharge pressure of the ventilation blower 104a such that the pressure as measured by the third flow rate, temperature and pressure sensor 113 is maintained at about 10 cm $H_2O$ to about 15 cm $H_2O$ during inspiration. In this embodiment, the computer system 119 controlled ventilation drive system 104 provides the required flow rate and 10 cm $H_2O$ to about 15 cm $H_2O$ pressure control of the inspiratory section gases to the patient at the patient connector tube 108, independent of the control and operation of the circulation flow system 102, which provides a computer system 119 controlled flow of the circulating gases from the expiratory section 101 to the inspiratory section 103 of the circulating loop. The circulation flow system 102 is computer system 119 controlled and operates independently of the ventilation drive system 104 to provide positive end-expiratory pressure control and ventilation control at the patient connector tube 108, from where the inspiratory section gases are inhaled by the patient, without the use of a proportional valve.

In an embodiment as exemplarily illustrated in FIG. 1, the anesthesia delivery and ventilation system 100 further comprises at least one elastic mixing reservoir 109 in fluid communication with the circulation flow system 102 and the fresh gas supply system 107 via a connector element 110. The volume of the elastic mixing reservoir 109 is, for example, about 2.5 liters when inflated to a maximum. The volume of the inspiratory section gases inspired by a patient is, for example, about 0.5 liters. The volume of the elastic mixing reservoir 109 in the deflated condition is the volume when inflated minus the inspired volume. The elastic mixing reservoir 109 is constructed, for example, from silicone rubber. The second end 101b of the expiratory section 101 is operably connected to the elastic mixing reservoir 109 via the connector element 110. The connector element 110 comprises a stopper 116, an inlet tube 117, and an outlet tube 118 as disclosed in the detailed description of FIGS. 2A-2B. The elastic mixing reservoir 109 is, for example, a flexible container or a flexible receptacle that expands and contracts depending on the volume of residual gases, the expiratory section gases, fresh gases, and/or the inspiratory section gases contained, fed into, or discharged from the elastic mixing reservoir 109.

When the expiratory section gases and the fresh gases enter the elastic mixing reservoir 109, the elastic mixing reservoir 109 expands. When the volume of the expiratory section gases, the fresh gases, and the residual gases in the elastic mixing reservoir 109 decreases, the elastic mixing reservoir 109 contracts. The elastic mixing reservoir 109, in fluid communication with the circulation flow system 102 and the fresh gas supply system 107 via the connector element 110, receives and mixes the circulating expiratory section gases from the circulation flow system 102 and the fresh gases from the fresh gas supply system 107 with residual gases contained in the elastic mixing reservoir 109. The connector element 110 comprising the inlet tube 117 and the outlet tube 118 exemplarily illustrated in FIGS. 2A-2B, ensures that the fresh gases from the fresh gas supply system 107 are mixed with the expiratory section gases that are substantially free of carbon dioxide from the circulation flow system 102 to reach the required composition of gases for delivery to and inspiration by the patient.

In the absence of the elastic mixing reservoir 109, a large volume of residual gases retained in an elastic non-mixing reservoir (not shown) is bypassed by the circulation flow, thereby precluding mixing of the expiratory section gases circulated by the circulation blower 102a of the circulation flow system 102 with the fresh gases and the residual gases retained in the elastic non-mixing reservoir. When the ventilation drive system 104 delivers the inspiratory section gases for inhalation by the patient, a certain volume of the residual gases retained in the elastic non-mixing reservoir, approximately equal to the volume of the inspiratory section gases inspired by the patient, is mixed with the fresh gases and the expiratory section gases that are circulated by the circulation blower 102a of the circulation flow system 102 in the anesthesia delivery and ventilation system 100. After the patient breathes in the inspiratory section gases with a required gas concentration, the non-uniformly mixed residual gases result in alteration of the gas concentration of the inspiratory section gases available for the next breath by the patient. The elastic mixing reservoir 109 mixes the fresh gases from the fresh gas supply system 107 and the expiratory section gases from the circulation flow system 102 with the residual gases retained in the elastic mixing reservoir 109 to produce the inspiratory section gases.

As an example of the change in the gas concentration in the circulating loop due to improper mixing of residual gases with the fresh gases and the expiratory section gases, assume that at a certain point in time, the inspiratory section gases and the expiratory section gases comprise air and the inspiratory section gases and the expiratory section gases are uniform throughout the circulating loop. The capacity of the elastic mixing reservoir 109 is, for example, about 2.5 liters, and the capacity of the remaining portion of the circulating loop is, for example, 2.5 liters. Assume that the volume of the inspiratory section gases delivered to a patient for ventilation, hereinafter referred to as "ventilation volume", is, for example, about 500 milliliters (ml), and the set oxygen concentration is increased, for example, to 50% oxygen. In an embodiment, a first feedback control loop for oxygen in the computer system 119 opens a gas inlet valve for oxygen from the gas inlet valves 107a in the fresh gas supply system 107 until the oxygen concentration reaches, for example, about 50% oxygen as measured by the breathing gas concentration sensor 114b, and then closes the gas inlet valve for oxygen. In the elastic mixing reservoir 109, without good mixing, for example, only about 3000 ml of gases in the circulating loop comprising 2500 ml of circulating gases and fresh gases, and 500 ml of the ventilation volume are refreshed with extra oxygen to reach 50% oxygen concentration. The remaining volume, for example, 2000 ml, of residual gases in the elastic mixing reservoir 109 is unmixed and is therefore at, for example, 21% oxygen concentration. Then, when there is a sudden change in the ventilation volume, for example, when the patient breathes a sigh, thereby increasing the ventilation volume to 1000 ml, the anesthesia delivery and ventilation system 100 supplies the additional 500 ml of inspiratory section gases from the elastic mixing reservoir 109, which, without proper mixing would still be at about 21% oxygen concentration. The additional 500 ml of inspiratory section gases at 21% oxygen concentration mixes with the previous 3000 ml of gases in the circulating loop at 50%, thereby decreasing the oxygen concentration of the gases in the circulation loop to about 46% according to the following equation:

$$\{(3000\ ml \times 50\%) + (500\ ml \times 21\%)\} \div (3500\ ml) = 0.458 = 45.8\%$$

Proper mixing of the fresh gases, the circulating gases, and the residual gases in the elastic mixing reservoir 109 achieves about 50% oxygen concentration in the residual gases in the elastic mixing reservoir 109. The first feedback control loop for oxygen in the computer system 119 adjusts the gas inlet valve for oxygen from the gas inlet valves 107a in the fresh gas supply system 107 such that the gas concentration measured by the breathing gas concentration sensor 114b is 50% oxygen concentration in a condition of complete mixing. Therefore, there is no drop in the oxygen concentration due to sudden changes in the ventilation volume. The fresh gases from the fresh gas supply system 107, the circulating gases circulated by the circulation flow system 102, and the residual gases in the elastic mixing reservoir 109 are mixed with one another in the elastic mixing reservoir 109 and transported to the inspiratory section 103.

The inspiratory section 103 is operably connected to and in fluid communication with the elastic mixing reservoir 109 via the connector element 110. The inspiratory section 103 comprises a first end 103a and a second end 103b. The first end 103a of the inspiratory section 103 is operably connected to and in fluid communication with the connector element 110. The second end 103b of the inspiratory section 103 is operably connected to and in fluid communication with the patient connector tube 108. The inspiratory section 103 receives the mixed gases comprising the circulating gases, the fresh gases, and the residual gases from the elastic mixing reservoir 109 via the connector element 110. Mixed gases refer to the gases from the expiratory section 101 mixed with the fresh gases from the fresh gas supply system 107 that are delivered to the inspiratory section 103. In an embodiment, the mixed gases comprise the residual gases in the elastic mixing reservoir 109 mixed with the gases from the expiratory section 101 and the fresh gases from the fresh gas supply system 107. The mixed gases are optionally infused with an inhalational anesthetic agent.

The ventilation drive system 104 is operably positioned at a predetermined location 103c in the inspiratory section 103 for delivering the mixed gases comprising oxygen and other gases optionally infused with the inhalational anesthetic agent to the patient at the patient connector tube 108, and for providing ventilation control to the patient when the lungs of the patient are ventilated. The ventilation drive system 104, which is controlled by the computer system 119, transports the flow of inspiratory section gases received from the elastic mixing reservoir 109 from the first end 103a of the inspiratory section 103 to the second end 103b of the inspiratory section 103 and thereafter to the patient connector tube 108, through the ventilation blower 104a for inhalation by the patient, and to provide controlled inhalation and/or exhalation ventilation patterns. As used herein, "ventilation patterns" comprise, for example, timing control for inspiration and expiration, a controlled pressure or a controlled flow pattern during inspiration, a controlled pressure pattern during expiration, etc. An example of the capacity of the ventilation blower 104a is about 150 liters per minute, peak flow. The ventilation drive system 104 is positioned between the first end 103a of the inspiratory section 103 and the second end 103b of the inspiratory section 103. If the patient requires an inhalational anesthetic agent, the anesthesia delivery system 105 infuses an anesthetic agent in a liquid state into the inspiratory section gases in the inspiratory section 103 where the liquid anesthetic agent vaporizes and mixes with the inspiratory section gases delivered by the ventilation drive system 104. The ventilation drive system 104 delivers a portion of the inspiratory section gases with the vaporized anesthetic agent from the anesthesia delivery system 105 to the patient connector tube 108 for inhalation by the patient. The ventilation drive system 104 delivers the remaining portion of the inspiratory section gases optionally infused with the inhalational anesthetic agent to the expiratory section 101.

The speed in rotations per minute (rpm) of the ventilation blower 104a and the corresponding flow rate of the inspiratory section gases through the ventilation blower 104a is controlled by the computer system 119, based on the first feedback control loop from the third flow rate, temperature and pressure sensor 113 to the computer system 119. The speed in rpm of the circulation blower 102a and the corresponding flow rate of the expiratory section gases through the circulation blower 102a are controlled by the computer system 119, based on the second feedback control loop that is defined by a combination of the first flow rate, temperature and pressure sensor 111, the second flow rate, temperature and pressure sensor 112, the third flow rate, temperature and pressure sensor 113, and the fourth flow rate, temperature and pressure sensor 115c to the computer system 119.

The circulation blower 102a is controlled by the computer system 119 for circulating a controlled, continuous flow of expiratory section gases in the expiratory section 101 from the first end 101a of the expiratory section 101 towards the second end 101b of the expiratory section 101. The computer system 119 controls the speed of the circulation blower 102a by either increasing or decreasing electrical power supplied to the circulation blower 102a to maintain the circulation flow rate of the expiratory section gases in the expiratory section 101 from the first end 101a of the expiratory section 101 towards the second end 101b of the expiratory section 101 at a preset flow rate. In an embodiment, the computer system 119 calculates the circulation flow by comparing the flow rates measured by the flow rate, temperature and pressure sensors 111, 112, 113, and 115*c*. For example, the circulation flow rate is the difference between the flow rate measured by the flow rate, temperature and pressure sensor 112 and the sum of flow rates measured by the flow rate, temperature and pressure sensors 113 and 115*c*. The flow rate of the expiratory section gases and the inspiratory section gases in the circulating loop is, for example, about 60 liters per minute. The flow rate of the inspiratory section gases inhaled by a patient is, for example, about 4 liters per minute to about 8 liters per minute.

The anesthesia delivery system 105 is operably connected to the inspiratory section 103 and is in fluid communication with the inspiratory section 103. The anesthesia delivery system 105 comprises an anesthesia delivery tube 105*a*, an anesthesia container 105*b* for storing an inhalational anesthetic agent, and a pump 105*c* for pumping the inhalational anesthetic agent into the inspiratory section 103. The anesthesia delivery tube 105*a* infuses the inhalational anesthetic agent into the inspiratory section 103 that contains the inspiratory section gases from the elastic mixing reservoir 109 transported by the ventilation blower 104*a*. The required inhalational anesthetic agent is filled in the anesthesia container 105*b* and mounted on the inspiratory section 103 of the anesthesia delivery and ventilation system 100. The anesthesia container 105*b* is maintained at a predefined pressure, for example, about 9 cm $H_2O$ that is higher than the pressure in the anesthesia delivery and ventilation system 100. A precision valve (not shown) in the anesthesia delivery tube 105*a* injects a small amount of the liquid anesthetic agent required in the inspiratory section gases in the inspiratory section 103, for example, in the order of micro liters into the inspiratory section 103 based on a feedback control loop controlled by the computer system 119.

Since the volume of the liquid anesthetic agent is of the order of micro liters and there is a continuous flow of the inspiratory section gases from the elastic mixing reservoir 109 along the inspiratory section 103, the liquid anesthetic agent vaporizes in the inspiratory section 103 at the point of injection. The precision valve in the anesthesia delivery tube 105*a* is controlled by the computer system 119 to achieve the required concentration of the inhalational anesthetic agent in the inspiratory section gases. A feedback control loop in the computer system 119 is used to control the precision valve based on the concentration of the inhalational anesthetic agent in the inspiratory section gases and the expiratory section gases. The concentration of the inhalational anesthetic agent required in the inspiratory section gases can be set in the feedback control loop in the computer system 119 to achieve the desired concentration of the inhalational anesthetic agent prior to inspiration and prior to or at the end of expiration by the patient. The concentration of the inhalational anesthetic agent prior to inspiration by the patient refers to the concentration of the inhalational anesthetic agent in the inspiratory section gases immediately prior to inspiration by the patient. Also, the concentration of the inhalational anesthetic agent prior to expiration by the patient refers to the concentration of the inhalational anesthetic agent in the expiratory section gases immediately prior to expiration by the patient. Also, the concentration of the inhalational anesthetic agent at the end of expiration refers to the concentration of the inhalational anesthetic agent in the expiratory section gases immediately after expiration. The pump 105*c* of the anesthesia delivery and ventilation system 100 pumps the inhalational anesthetic agent into the inspiratory section 103 and injects the inhalational anesthetic agent of, for example, a few micro liters at a pressure above the pressure of the inspiratory section gases in the inspiratory section 103. The inspiratory section 103 transports the inspiratory section gases received from the elastic mixing reservoir 109 along with the injected inhalational anesthetic agent to the patient through the patient connector tube 108.

In an embodiment, the first flow rate, temperature and pressure sensor 111 is positioned at the inlet tube 117 of the connector element 110. The first flow rate, temperature and pressure sensor 111 measures the flow rate of the expiratory section gases and the fresh gases, if any, injected into the elastic mixing reservoir 109. The second flow rate, temperature and pressure sensor 112 is positioned at the outlet tube 118 of the connector element 110. The second flow rate, temperature and pressure sensor 112 measures the flow rate of the inspiratory section gases flowing out of the elastic mixing reservoir 109. The difference between the flow rate of the expiratory section gases and the fresh gases flowing into the elastic mixing reservoir 109 as measured by the first flow rate, temperature and pressure sensor 111 and the flow rate of the inspiratory section gases flowing out of the elastic mixing reservoir 109 as measured by the second flow rate, temperature and pressure sensor 112 provides the change in volume of the gases in the elastic mixing reservoir 109. The flow rate is measured in units of volume per unit time. For example, when fresh gases at a flow rate of 0.5 liters per minute enter the elastic mixing reservoir 109 but do not leave the elastic mixing reservoir 109, then the increase in volume of the gases in the elastic mixing reservoir 109 in one minute is 0.5 liters. When the gas inlet valves 107*a* of the fresh gas supply system 107 are opened, additional fresh gases flow into the elastic mixing reservoir 109. The volume of the additional fresh gases flowing into the elastic mixing reservoir 109 can be calculated by the changes in the volume of the gases in the elastic mixing reservoir 109 over the time the gas inlet valves 107*a* are opened.

The third flow rate, temperature and pressure sensor 113 positioned at the patient connector tube 108 measures the volume of the inspiratory section gases inspired and the volume of the expiratory section gases expired by a patient. In an embodiment, the computer system 119 controls the timing of measurements by the third flow rate, temperature and pressure sensor 113 for measuring the volume of the inspiratory section gases and then the volume of the expiratory section gases. The fourth flow rate, temperature and pressure sensor 115*c* positioned at an exhaust port 115*d* in the expiratory section 101 measures the volume of the expiratory section gases vented to the environment when pressure limiting valves 115*a* and 115*b* connected to the expiratory section 101 as exemplarily illustrated in FIG. 1, are opened. The measurement of the volume of the expiratory section gases vented to the environment enables an operator of the anesthesia delivery and ventilation system 100 to regulate the flow rate and/or pressure of the circulating gases at various sections of the anesthesia delivery and ventilation system 100. The breathing gas concentration sensors 114*a* and 114*b* measure the concentrations of oxygen ($O_2$), carbon dioxide ($CO_2$), xenon, and the inhalational anesthetic agent at their respective locations exemplarily illustrated in FIG. 1. That is, when concentrations of $O_2$ drop below a set point, the fresh gas supply system 107 supplies an additional volume of $O_2$. Similarly, the concentrations of the other gases, for example, xenon, the anesthetic agent, etc., in the inspiratory section gases are regulated. At the end of expiration and before the next inspiration by the patient, the pressure at the first flow rate, temperature and pressure sensor 111 is, for example, about 3 cm $H_2O$. The pressure at the second flow rate, temperature and pressure sensor 112 is slightly lower, for example, about 1 cm $H_2O$, and the pressure at the third flow rate, temperature and pressure sensor 113 is the positive end-expiratory pressure. The positive end-expiratory pressure is typically set between about 2 cm $H_2O$ to about 10 cm $H_2O$. The computer system 119 maintains the positive end-expiratory pressure at about 2 cm $H_2O$ to about 10 cm $H_2O$ by controlling the ventilation blower 104a. By controlling the ventilation blower 104a, the computer system 119 also compensates for the pressure change across the circulation blower 102a and the elastic mixing reservoir 109. The ventilation blower 104a can increase the pressure from the pressure at the second flow rate, temperature and pressure sensor 112 to the pressure at the third flow rate, temperature and pressure sensor 113. The circulation flow system 102 produces the pressure measured at the first flow rate, temperature and pressure sensor 111. The pressure measured at the second flow rate, temperature and pressure sensor 112 is the pressure after a small drop in pressure at the elastic mixing reservoir 109. The pressure generated by the ventilation drive system 104 is read at the third flow rate, temperature and pressure sensor 113. Fresh gas is supplied to the expiratory section 101 at a pressure of about 2039 cm $H_2O$. In an embodiment, the fresh gas supply pressure is adjusted by a pressure reducer (not shown) positioned proximal to the gas inlet valves 107a of the fresh gas supply system 107.

In a fully closed system, when the gas inlet valves 107a positioned in the fresh gas supply system 107 are closed, during inspiration, the flow rate measured by the second flow rate, temperature and pressure sensor 112 is a sum of the flow rate of the inspiratory section gases entering the lungs of the patient as measured by the third flow rate, temperature and pressure sensor 113 and the flow rate of the expiratory section gases through the circulation flow system 102 as measured by the first flow rate, temperature and pressure sensor 111. The flow rate of the inspiratory section gases to the patient's lungs is, for example, about 4 liters per minute to about 8 liters per minute. The flow rate of the expiratory section gases is, for example, about 45 liters per minute to about 65 liters per minute. During expiration, the flow rate measured by the first flow rate, temperature and pressure sensor 111 is the flow rate of the fresh gases, if the gas inlet valves 107a are opened, and the expiratory section gases going into the elastic mixing reservoir 109. The flow rate of the inspiratory section gases from the elastic mixing reservoir 109 to the inspiratory section 103 is different during inspiration and expiration. During inspiration, the flow rate of the inspiratory section gases from the elastic mixing reservoir 109 to the inspiratory section 103 is the sum of the flow rate through the circulation blower 102a of the circulation flow system 102 and the flow rate of the flow of the inspiratory section gases to the lungs of the patient. During expiration, the flow rate through the circulation blower 102a is the sum of the flow rate of inspiratory section gases from the elastic mixing reservoir 109 to the inspiratory section 103 and the flow rate of the expiratory section gases from the lungs of the patient. The circulation flow rate is, for example, about 45 liters per minute to about 65 liters per minute and the flow rate to the lungs is about 4 liters per minute to about 8 liters per minute. The flow rate expired by the patient is approximately equal to the flow rate inspired by the patient with some negligible differences due to gas exchange in the lungs.

The breathing gas concentration sensor 114a measures the concentration of various gases in the inspiratory section gases and the expiratory section gases. The breathing gas concentration sensor 114b measures the concentrations of gases in the inspiratory section gases. Consider an example of a mixture of oxygen ($O_2$), xenon, and an inhalational anesthetic agent in the expiratory section gases and the inspiratory section gases. In this example, during inspiration, assume that the breathing gas concentration sensors 114a and 114b measure the concentration of $O_2$ as 50%, the concentration of the inhalational anesthetic agent as 5%, and the concentration of xenon as 45% on a volumetric basis. During expiration, the concentrations of $O_2$, the inhalational anesthetic agent, and xenon as measured by the breathing gas concentration sensor 114a would be lower due to the presence of an additional gas, for example, carbon dioxide ($CO_2$), having a non-zero value varying, for example, from 0% to about 5%.

The pressure limiting valves 115a and 115b are positioned at the exhaust port 115d of the expiratory section 101 as exemplarily illustrated in FIG. 1, and control the maximum pressure to which a patient's lungs are subjected. The pressure limiting valves 115a and 115b are, for example, pop-off valves provided as a safety measure to limit the maximum pressure to which a patient's lungs are subjected. Generally, pressures above about 30 cm $H_2O$ to about 40 cm $H_2O$ are considered harmful for the patient's lungs. The upper limit can be set by an operator of the anesthesia delivery and ventilation system 100 as per an individual patient's lung status. In an embodiment, the maximum pressure to which the patient's lungs are subjected is checked by continuously monitoring the pressure as measured by the flow rate, temperature and pressure sensor 113 and opening the pressure limiting valve 115a if required. In an embodiment, the maximum pressure to which the patient's lungs are subjected is limited by using the pressure limiting valve 115b, which is a mechanical pressure limiting valve that uses a spring-loaded maximum pressure limiter. Both the embodiments can be implemented simultaneously in the anesthesia delivery and ventilation system 100 as exemplarily illustrated by the pressure limiting valves 115a and 115b in FIG. 1.

The ventilation blower 104a of the ventilation drive system 104 controls the pressure of the inspiratory section gases and the pressure of the expiratory section gases during inspiration and expiration. If the patient's inspiration pressure is above a set maximum pressure value, software implemented in the computer system 119 opens the pressure limiting valve 115a until the pressure returns to the set maximum pressure value. The maximum pressure value for the inspiratory section gas pressure at an inlet to the patient's lungs is, for example, about 20 cm $H_2O$ to about 30 cm $H_2O$. The inspiratory section gas pressure at the inlet to the patient's lungs is measured by the flow rate, temperature and pressure sensor 113. If there is a failure in the software in the computer system 119, the mechanical pressure limiting valve 115b is automatically activated to reduce the pressure in the anesthesia delivery and ventilation system 100 to the set maximum pressure value.

Before using the anesthesia delivery and ventilation system 100 disclosed herein, the anesthesia delivery and ventilation system 100 is prepared with the required concentration of inspiratory section gases, for example, oxygen and air. During a startup procedure, the patient connector tube 108 is closed to prevent any leakage of the inspiratory section gases from the patient connector tube 108 to the environment. A point of interconnection between the inspiratory section 103 and the patient connector tube 108 is also made airtight to prevent leakage of the inspiratory section gases. The circulation blower 102a of the circulation flow system 102 is turned on and run continuously. The speed of the ventilation blower 104a is controlled such that the pressure at the third flow rate, temperature and pressure sensor 113 is slightly above atmospheric pressure, for example, about 0.5 cm $H_2O$, to prevent ambient air from entering the anesthesia delivery and ventilation system 100. The first flow rate, temperature and pressure sensor 111 and the second flow rate, temperature and pressure sensor 112 positioned proximal to the elastic mixing reservoir 109 are used to monitor the flow rates of the expiratory section gases that are circulated in the expiratory section 101 and the inspiratory section gases that are transported in the inspiratory section 103 of the anesthesia delivery and ventilation system 100.

When there is no inspiration or expiration by a patient, the flow rates in the expiratory section 101 and the inspiratory section 103 are equal, for example, about 45 liters per minute to about 65 liters per minute. During inspiration by a patient, the flow rate in the inspiratory section 103 from the elastic mixing reservoir 109 downstream is changed by the flow of the inspiratory section gases to the lungs of the patient and is, for example, about 4 liters per minute to about 8 liters per minute. During expiration, the flow rate in the expiratory section 101 is changed by the flow of the gases exhaled from the lungs of the patient and is, for example, about 4 liters per minute to about 8 liters per minute. If required, an additional volume of fresh gases is transported from the fresh gas supply system 107 into the anesthesia delivery and ventilation system 100. The additional volume of fresh gases is proportional to the changes in the set gas concentrations in the anesthesia delivery and ventilation system 100. The additional volume of fresh gases is stored in the elastic mixing reservoir 109 until the maximum volume of the elastic mixing reservoir 109 is reached, which is about 2.5 liters. If the volume of the fresh gases fed into the circulating loop tries to increase the volume of the elastic mixing reservoir 109 beyond the maximum volume of the elastic mixing reservoir 109, the pressure limiting valve 115a opens to release the excess volume. The fresh gases mixed with the residual gases in the elastic mixing reservoir 109 and the expiratory section gases in combination with the infused anesthetic agent are inspired by the patient. The residual gases and the expiratory section gases are routed to the expiratory section 101 during expiration of the lung.

During startup, the anesthesia delivery and ventilation system 100 is filled, for example, with air and oxygen ($O_2$) to an adequate volume sufficient for ventilating the patient and providing a sufficient continuous flow of inspiratory section gases within the anesthesia delivery and ventilation system 100. The breathing gas concentration sensors 114a and 114b are positioned between the patient connector tube 108 and the ventilation drive system 104. The required concentrations of gases in the inspiratory section gases are obtained by controlling the flow of each of the gases from the fresh gas supply system 107. For example, if only air is in the anesthesia delivery and ventilation system 100 at a certain time, the feedback control loop in the computer system 119 opens a gas inlet valve for oxygen from the gas inlet valves 107a in the fresh gas supply system 107 until oxygen concentration reaches, for example, about 50% oxygen as measured by the breathing gas concentration sensor 114b, and then closes the gas inlet valve for oxygen. Depletion of $O_2$ in lungs of the patient is about 250 ml per minute when the patient is at rest. In an embodiment, a certain volume of the expiratory section gases expired by the patient is allowed to escape via the pressure limiting valve 115a to adjust for any excess pressure created in the circulating gases by the additional $O_2$ injected into the anesthesia delivery and ventilation system 100. To lower the concentration of $O_2$ in the anesthesia delivery and ventilation system 100, other gases, for example, air, xenon, etc., are fed into the anesthesia delivery and ventilation system 100 from the fresh gas supply system 107. Furthermore, if necessary, the pressure limiting valve 115a is opened to discharge the expiratory section gases expired by the patient and adjust for any excess pressure and/or volume created by the additional oxygen gas fed into the circulating loop.

The composition of the inspiratory section gases required for inspiration by the patient is obtained by controlling the flow of the fresh gases desired in the inspiratory section gases through the gas inlet valves 107a exemplarily illustrated in FIG. 1. In an embodiment, the gas inlet valves 107a are electromechanical valves, where an electrical signal voltage or current of a predetermined value keeps the gas inlet valves 107a open and another electrical signal voltage or current of another predetermined value closes the gas inlet valves 107a. The current or voltage values can vary, for example, from about 3 volts to about 60 volts. In an embodiment, the anesthesia delivery and ventilation system 100 implements a pulse width modulation technique to modify the opening and closing times of the gas inlet valves 107a of the individual fresh gas supply tubes 107b in the fresh gas supply system 107 as required. In an embodiment, the anesthesia delivery and ventilation system 100 comprises two sets of breathing gas concentration sensors 114a and 114b for each gas type, for example, oxygen, xenon, etc. One set of breathing gas concentration sensors 114a is positioned proximal to the patient connector tube 108 and the other set of breathing gas concentration sensors 114b is positioned between the anesthesia delivery system 105 and the patient connector tube 108.

Consider an example where the oxygen concentration measured by the breathing gas concentration sensor 114a or 114b is 21%. The breathing gas concentration sensor 114a measures the concentration of gases inspired and expired by the patient, which are different for inspiration and expiration. For example, the carbon dioxide ($CO_2$) concentration measured by the breathing gas concentration sensor 114a during inspiration is almost zero. During expiration, the $CO_2$ concentration measured by the breathing gas concentration sensor 114a increases from near zero at the start of expiration and reaches the maximum value at the end of expiration, for example, about 4% to about 5%. The breathing gas concentration sensor 114b measures concentrations of the circulating gases that circulate in the circulating loop and is almost the same during inspiration and expiration, except for small changes due to the absorption of oxygen in the lungs. For example, the $CO_2$ concentration measured by the breathing gas sensor 114b is near to zero during inspiration and expiration since the carbon dioxide ($CO_2$) absorbers 106a and 106b remove the $CO_2$ before the $CO_2$ reaches the breathing gas concentration sensor 114b. Consider an example of the concentrations of the inspiratory section gases in the anesthesia delivery and ventilation system 100 measured during a start-up of the anesthesia delivery and ventilation system 100. Sufficient concentrations of fresh gases, for example, air, oxygen, xenon, etc., are fed into the anesthesia delivery and ventilation system 100. A known volume of oxygen ($O_2$), for example, about 100 ml, is added to the inspiratory section gases in the anesthesia delivery and ventilator system 100. A new measurement of $O_2$ concentration performed by the breathing gas concentration sensor 114a or 114b is, for example, about 25%. The computer system 119 calculates the volume of the anesthesia delivery and ventilation system 100 using the difference in concentration and the added volume of $O_2$. In an embodiment, the computer system 119 performs the following calculation: system volume multiplied by the measured current gas concentration is equal to system volume plus additional gas volume multiplied by the measured new gas concentration. Since all the other variables are known, the system volume can be calculated. In an embodiment, the anesthesia delivery and ventilation system 100 includes additional parameters, for example, temperature, in the calculation.

Once the volume of the anesthesia delivery and ventilation system 100 has been calculated at startup, further changes in the volume, for example, due to addition of fresh gases, leakage, etc., are calculated by following the changes in the pressure, the temperature, and the flow rate measured by the first flow rate, temperature and pressure sensor 111, the second flow rate, temperature and pressure sensor 112, the third flow rate, temperature and pressure sensor 113, and the fourth flow rate, temperature and pressure sensor 115c. After the startup procedure, the patient connector tube 108 is connected to the patient. In an embodiment, two modes of flow are configured in the anesthesia delivery and ventilation system 100, namely, a pressure-controlled mode and a volume-controlled mode. The other modes are based on these two base modes of flow. In the pressure-controlled mode of flow, during inspiration, the airway pressure is maintained at the required inspiration pressure, and during expiration, the airway pressure is maintained at the positive end-expiratory pressure. In an embodiment, example values for inspiration pressure range from about 10 cm $H_2O$ to about 50 cm $H_2O$. In an embodiment, example values for positive end-expiratory pressure range from about 2 cm $H_2O$ to 20 cm $H_2O$. The pressure of the inspiratory section gases including the inhalational anesthetic agent at the patient connector tube 108, as measured by the third flow rate, temperature and pressure sensor 113, is the difference between the positive pressure produced by the ventilation blower 104a and the pressure due to the circulation blower 102a. The computer system 119 maintains the preset inspiration pressure, the expiration pressure, and the positive end-expiratory pressure at the patient connector tube 108 as indicated on the third flow rate, temperature and pressure sensor 113 by controlling the speed of the ventilation blower 104a. Consider an example where high concentrations of xenon in the inspiratory section gases increase the friction of the ventilation blower 104a, which cause a drop in the speed of the ventilation blower 104a. To maintain the same pressure, the computer system 119 increases electrical power supplied to the ventilation blower 104a.

In the volume controlled mode of flow, the flow rate of the inspiratory section gases including the inhalational anesthetic agent is kept constant or in a pattern such that that the required volume of the inspiratory section gases is delivered to the patient's lungs during inspiration. Expiration is passive, where the flow rate of the expiratory section gases is not controlled externally, with the airway pressure maintained at a set positive end-expiratory pressure value of about 2 cm $H_2O$ to about 10 cm $H_2O$. In the anesthesia delivery and ventilation system 100 disclosed herein, the ventilation blower 104a is controlled such that the flow rate of the inspiratory section gases as measured by the third flow rate, temperature and pressure sensor 113 is maintained at a set value, for example, about 4 liters per minute to about 8 liters per minute, during inspiration. Expiration in the volume controlled mode of flow is similar to expiration in the pressure-controlled mode of flow disclosed above with the pressure of the inspiratory section gases in the inspiratory section 103 of the circulating loop maintained at the set positive end-expiratory pressure value by controlling the ventilation blower 104a. In an example, the positive end-expiratory pressure value ranges from about 2 cm $H_2O$ to about 20 cm $H_2O$ and the positive end-expiratory pressure value is indicated and measured by the third flow rate, temperature and pressure sensor 113 at the end of expiration.

Figure 2A:
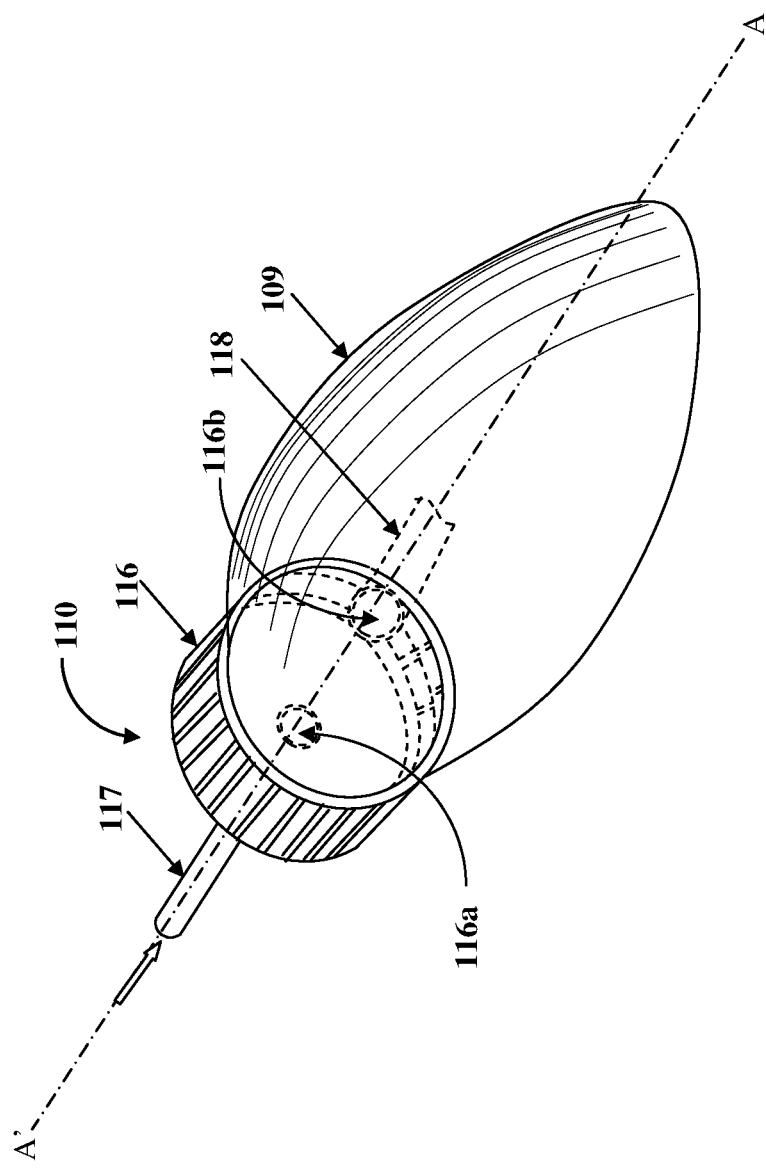
FIGS. 2A-2B exemplarily illustrate perspective views of a connector element of the anesthesia delivery and ventilation system.
Figure 2B:
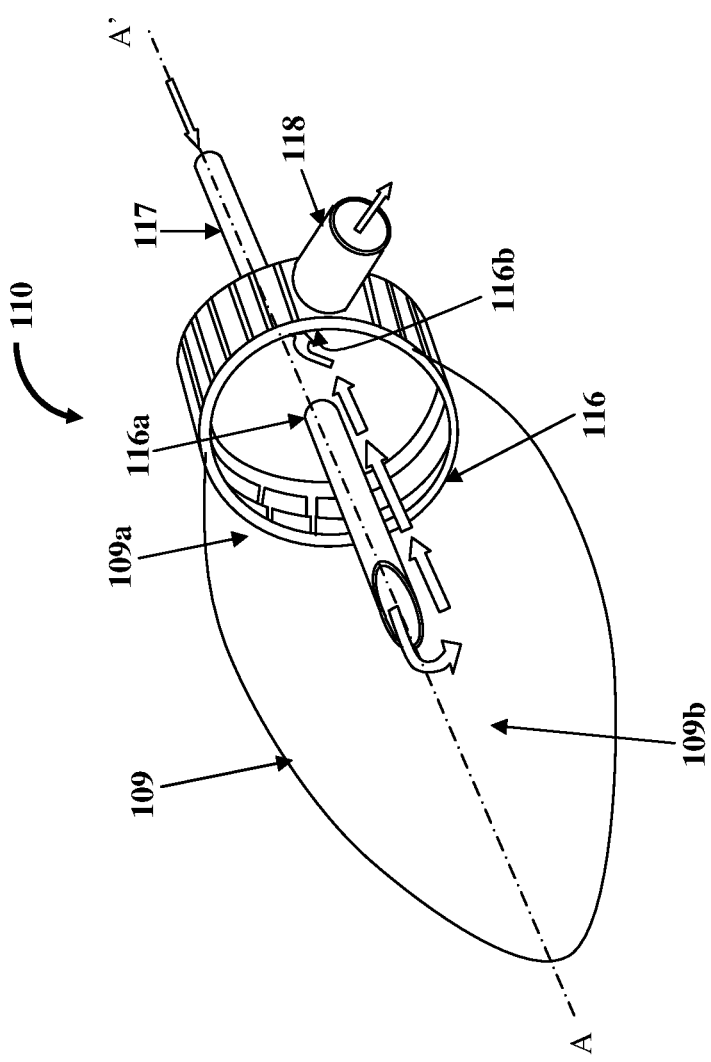

FIGS. 2A-2B exemplarily illustrate perspective views of the connector element 110 of the anesthesia delivery and ventilation system 100 exemplarily illustrated in FIG. 1. The connector element 110 comprises a stopper 116, an inlet tube 117, and an outlet tube 118. The inlet tube 117 is in fluid communication with the expiratory section 101 and operably connected to the second end 101b of the expiratory section 101 exemplarily illustrated in FIG. 1, for transporting the circulating gases from the circulation flow system 102 exemplarily illustrated in FIG. 1, and the fresh gases from the fresh gas supply system 107 exemplarily illustrated in FIG. 1, to the elastic mixing reservoir 109. The inlet tube 117 is in fluid communication with the elastic mixing reservoir 109 and is positioned at an angle, for example, 90° with respect to the outlet tube 118. The stopper 116 is positioned on an upper end 109a of the elastic mixing reservoir 109 for containing the circulating gases from the circulation flow system 102, the fresh gases from the fresh gas supply system 107, and the residual gases in the elastic mixing reservoir 109. The stopper 116 comprises a first opening 116a and a second opening 116b. The expiratory section gases from the expiratory section 101 and the fresh gases from the fresh gas supply system 107 are fed into the elastic mixing reservoir 109 through the inlet tube 117 inserted into the first opening 116a of the stopper 116. The first opening 116a is positioned about a central axis AA' of the stopper 116. The second opening 116b is positioned transaxial to the central axis AA' of the first opening 116a in the stopper 116. That is, the second opening 116b is positioned substantially perpendicular to the central axis AA' of the stopper 116.

As exemplarily illustrated in FIG. 1 and FIGS. 2A-2B, the inlet tube 117 extends to the lower section 109b of the elastic mixing reservoir 109. The mixture of circulating gases comprising the expiratory section gases from the circulation flow system 102 and the fresh gases from the fresh gas supply system 107 is fed into the lower section 109b of the elastic mixing reservoir 109, which contains the residual gases, through the inlet tube 117. The recirculated expiratory section gases from the circulation blower 102a of the circulation flow system 102 exemplarily illustrated in FIG. 1, the fresh gases from the fresh gas supply system 107, and the residual gases in the elastic mixing reservoir 109 mix in the elastic mixing reservoir 109. The design of the connector element 110 exemplarily illustrated in FIGS. 2A-2B, ensures uniform mixing of the circulating gases, the fresh gases, and the residual gases in the elastic mixing reservoir 109. The outlet tube 118 is inserted into the second opening 116b of the stopper 116 and positioned substantially perpendicular to the inlet tube 117. The outlet tube 118 is in fluid communication with the elastic mixing reservoir 109 and is operably connected to the first end 103a of the inspiratory section 103 as exemplarily illustrated in FIG. 1. The outlet tube 118 receives the mixed gases from the elastic mixing reservoir 109 and transports the mixed gases to the inspiratory section 103. In the absence of the elastic mixing reservoir 109, surplus expiratory section gases and fresh gases will not be mixed properly and a large volumetric percent of the expiratory section gases or the fresh gases will be bypassed to the inspiratory section gases flowing in the inspiratory section 103. When ventilation starts, there will be a substantial change in the concentration of the resulting fresh gases and expiratory section gases from the previous gas concentration value. That is, the concentration of $O_2$, xenon, $CO_2$, etc., in the inspiratory section gases will be different from the concentration of $O_2$, xenon, $CO_2$, etc., in the expiratory section gases circulated by the circulation flow system 102 due to the previously unmixed volume of residual gases with the fresh gases retained in the inspiratory section 103.

Figure 3:
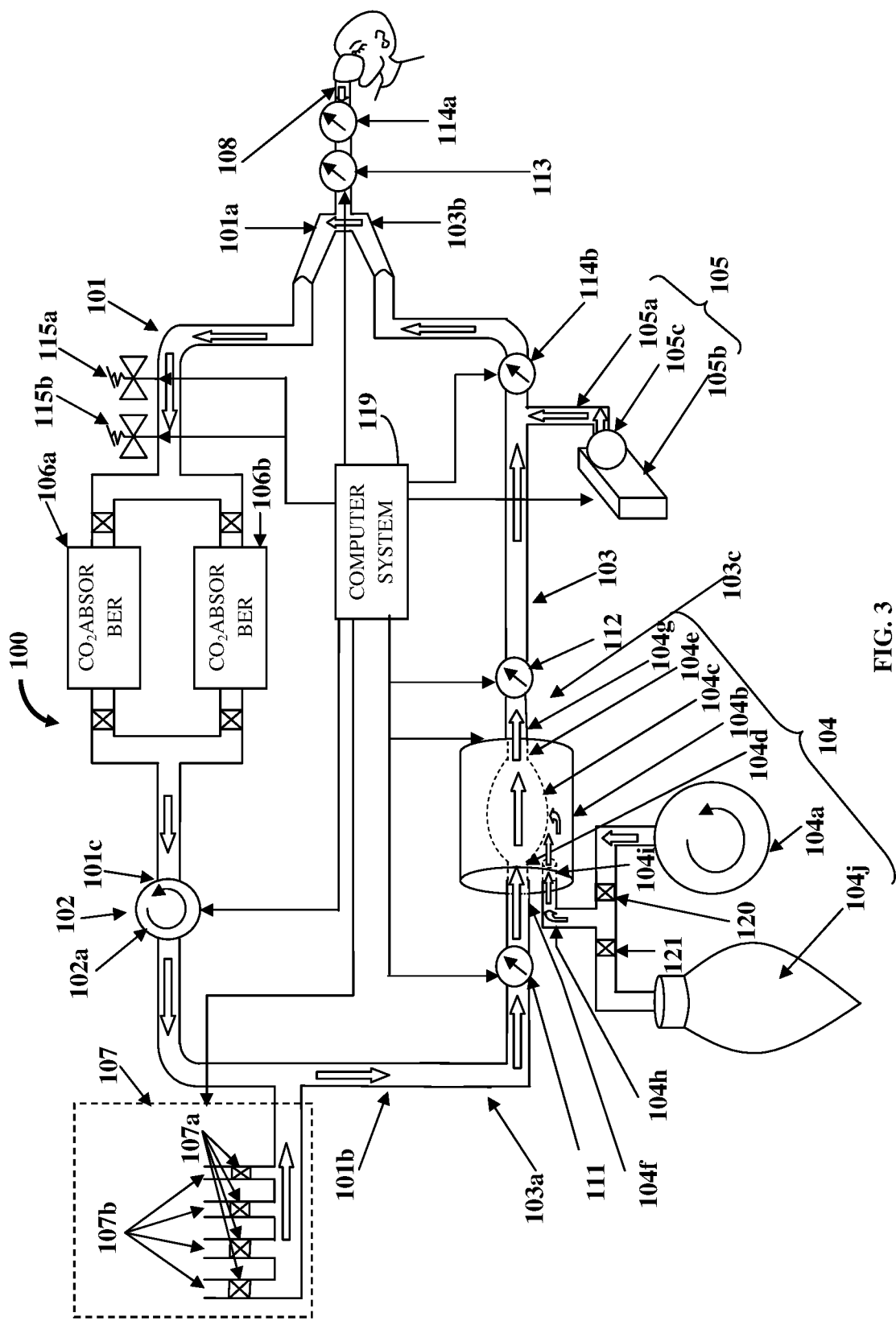
FIG. 3 exemplarily illustrates an embodiment of the anesthesia delivery and ventilation system.

FIG. 3 exemplarily illustrates an embodiment of the anesthesia delivery and ventilation system 100. In this embodiment, the anesthesia delivery and ventilation system 100 disclosed herein comprises an expiratory section 101, a circulation flow system 102, an inspiratory section 103, a ventilation drive system 104, and an anesthesia delivery system 105. The expiratory section 101 comprises a first end 101a and a second end 101b. The first end 101a of the expiratory section 101 is operably connected to a patient connector tube 108 for receiving gases exhaled by a patient via the patient connector tube 108 and gases bypassing inhalation and transported directly into the expiratory section 101 from the inspiratory section 103. The second end 101b of the expiratory section 101 is operably connected proximal to a fresh gas supply system 107 for receiving fresh gases, for example, oxygen, xenon, air, etc., for increasing the concentration of the received gases to a gas component level required to be maintained in the inspiratory section 103. A patient breathes from or into the patient connector tube 108. The patient connector tube 108 receives the gases exhaled by the patient. In an embodiment, the expiratory section gases comprising carbon dioxide are treated by passing the expiratory section gases through one or more carbon dioxide absorbers 106a and 106b. The carbon dioxide absorbers 106a and 106b are positioned between the first end 101a of the expiratory section 101 and the second end 101b of the expiratory section 101. The treated expiratory section gases flow into the circulation flow system 102. The circulation flow system 102 is operably positioned at a predetermined location 101c in the expiratory section 101. The circulation flow system 102 circulates the expiratory section gases towards the inspiratory section 103 of the anesthesia delivery and ventilation system 100. The fresh gases from the fresh gas supply system 107 mix with the expiratory section gases circulated by the circulation flow system 102 proximal to the second end 101b of the expiratory section 101.

In the embodiment exemplarily illustrated in FIG. 3, the circulation flow system 102 of the anesthesia delivery and ventilation system 100 comprises a circulation blower 102a. The circulation blower 102a is operably positioned at a predetermined location 101c in the expiratory section 101 for circulating the expiratory section gases in the expiratory section 101 substantially free of carbon dioxide towards the second end 101b of the expiratory section 101. The second end 101b of the expiratory section 101 receives the expiratory section gases from the circulation flow system 102 and the fresh gases from the fresh gas supply system 107. The inspiratory section 103 is in fluid communication with the circulation flow system 102 and the fresh gas supply system 107 via the second end 101b of the expiratory section 101. The first end 103a of the inspiratory section 103 is proximal to and in fluid communication with the second end 101b of the expiratory section 101. The second end 103b of the inspiratory section 103 is operably connected to the patient connector tube 108. The inspiratory section 103 receives the inspiratory section gases from an elastic ventilation and mixing reservoir 104c of the ventilation drive system 104 as exemplarily illustrated in FIG. 3.

The ventilation drive system 104 is operably positioned at a predetermined location 103c in the inspiratory section 103 for delivering the mixed gases comprising oxygen and other gases from the elastic ventilation and mixing reservoir 104c optionally infused with an inhalational anesthetic agent to the patient and for providing ventilation control to the patient when the lungs of the patient are ventilated. In the embodiment exemplarily illustrated in FIG. 3, the ventilation drive system 104 comprises a ventilation blower 104a, a ventilation housing 104b, the elastic ventilation and mixing reservoir 104c, an inlet ventilation tube 104f, an outlet ventilation tube 104g, and an elastic manual ventilation bag 104j. The ventilation housing 104b comprises multiple openings, for example, 104i, 104m, and 104n as exemplarily illustrated in FIG. 4D. The ventilation housing 104b accommodates the elastic ventilation and mixing reservoir 104c. The elastic ventilation and mixing reservoir 104c receives the expiratory section gases from the circulation flow system 102 and the fresh gases from the fresh gas supply system 107.

The inlet ventilation tube 104f and the outlet ventilation tube 104g are connected to opposing ends 104d and 104e of the elastic ventilation and mixing reservoir 104c within the ventilation housing 104b. The inlet ventilation tube 104f and the outlet ventilation tube 104g of the elastic ventilation and mixing reservoir 104c are positioned at, for example, 180° with respect to each other. The inlet ventilation tube 104f is inserted through one opening 104m of the ventilation housing 104b as exemplarily illustrated in FIG. 4D. The inlet ventilation tube 104f is in fluid communication with the circulation flow system 102 and the fresh gas supply system 107 via the second end 101b of the expiratory section 101 for receiving the expiratory section gases from the expiratory section 101 mixed with the fresh gases from the fresh gas supply system 107 and transporting the expiratory section gases from the circulation flow system 102 and the fresh gases from the fresh gas supply system 107 to the elastic ventilation and mixing reservoir 104c. The outlet ventilation tube 104g exits through another opening 104n in the ventilation housing 104b exemplarily illustrated in FIG. 4D. The outlet ventilation tube 104g is in fluid communication with the inspiratory section 103 for transporting the inspiratory section gases from the elastic ventilation and mixing reservoir 104c to the second end 103b of the inspiratory section 103.

The ventilation blower 104a is operably connected to the ventilation housing 104b and is isolated from the elastic ventilation and mixing reservoir 104c. The ventilation blower 104a is in fluid communication with the ventilation housing 104b via a tube 104h inserted through the opening 104i of the ventilation housing 104b. The ventilation blower 104a transports the inspiratory section gases received in the elastic ventilation and mixing reservoir 104c through the inspiratory section 103 of the circulating loop. The elastic manual ventilation bag 104j is in fluid communication with the ventilation blower 104a and is operably connected to the ventilation housing 104b. The elastic manual ventilation bag 104j and the ventilation blower 104a are selectively operated by opening and closing valves 121 and 120 respectively. The elastic manual ventilation bag 104j is operated manually and transports the inspiratory section gases received in the elastic ventilation and mixing reservoir 104c through the inspiratory section 103. The elastic manual ventilation bag 104j is isolated from the elastic ventilation and mixing reservoir 104c and is not in fluid communication with the elastic ventilation and mixing reservoir 104c.

The anesthesia delivery and ventilation system 100 exemplarily illustrated in FIG. 3, replaces an in-line blower used in conventional anesthesia delivery systems with the ventilation drive system 104. Hence, a turbine of the in-line blower is not in contact with breathing gases in the circulating loop, thereby precluding the need for sterilization of the turbine. In an embodiment, the elastic ventilation and mixing reservoir 104c is integrated in the ventilation drive system 104 and is enclosed in the ventilation housing 104b with a removable end face (not shown) for removing the elastic ventilation and mixing reservoir 104c for replacement with another elastic ventilation and mixing reservoir 104c. After replacing the elastic ventilation and mixing reservoir 104c, the removable end face can be clamped tightly to the ventilation housing 104b since there are no moving parts such as a turbine. Hence, the embodiment of the anesthesia delivery and ventilation system 100 exemplarily illustrated in FIG. 3, is less prone to leakage of gases because only the elastic ventilation and mixing reservoir 104c is in contact with the inspiratory section gases and the expiratory section gases, and therefore can be easily disinfected and sterilized. An operator of the anesthesia delivery and ventilation system 100 uses the elastic manual ventilation bag 104j to ventilate the patient manually if the operator elects to use manual ventilation. Typically, the elastic manual ventilation bag 104j is used during the process of connecting the patient to the anesthesia delivery and ventilation system 100 or when the ventilation blower 104a fails. During manual ventilation, the ventilation blower 104a is isolated by closing the valve 120 and opening the valve 121. Then, on pressing the elastic manual ventilation bag 104j, the residual gases in the elastic ventilation and mixing reservoir 104c are transported through the inspiratory section 103. When the elastic manual ventilation bag 104j is released, the patient's lungs enter the expiration phase. Furthermore, during manual ventilation, the ventilation blower 104a can be included by also opening the valve 120 to provide additional incremental pressure when the elastic manual ventilation bag 104j is manually used. During automatic ventilation, the elastic manual ventilation bag 104j is isolated by closing the valve 121.

Either the elastic manual ventilation bag 104j or the ventilation blower 104a or both exert a pressure on the elastic ventilation and mixing reservoir 104c to transport the inspiratory section gases contained in the elastic ventilation and mixing reservoir 104c through the inspiratory section 103. Since the ventilation blower 104a and the elastic manual ventilation bag 104j are isolated from inspiratory section gases and the expiratory section gases, only the elastic ventilation and mixing reservoir 104c needs to be disinfected or sterilized or disposed. The anesthesia delivery tube 105a of the anesthesia delivery system 105 is positioned between the first end 103a of the inspiratory section 103 and the second end 103b of the inspiratory section 103. The anesthesia delivery tube 105a is in fluid communication with the ventilation drive system 104, and optionally infuses the inspiratory section gases in the inspiratory section 103 with the required amount of an inhalational anesthetic agent contained in the anesthesia container 105b using the pump 105c of the anesthesia delivery system 105 as disclosed in the detailed description of FIG. 1. The anesthesia delivery and ventilation system 100 delivers the circulating inspiratory section gases optionally infused with the inhalational anesthetic agent to the patient connector tube 108 for inhalation by the patient as exemplarily illustrated in FIG. 3.

The anesthesia delivery and ventilation system 100 further comprises one or more pressure-limiting valves 115a and 115b as exemplarily illustrated in FIG. 3. The pressure-limiting valves 115a and 115b function as disclosed in the detailed description of FIG. 1. Furthermore, the anesthesia delivery and ventilation system 100 comprises a first flow rate, temperature and pressure sensor 111, a second flow rate, temperature and pressure sensor 112, a third flow rate, temperature and pressure sensor 113, and breathing gas concentration sensors 114a and 114b as disclosed in the detailed description of FIG. 1. The flow rate, temperature and pressure sensors 111, 112, and 113 measure the flow rate, temperature, and pressure of the fresh gases, the expiratory section gases, the inspiratory section gases, and the inhalational anesthetic agent. The breathing gas concentration sensors 114a and 114b measure the concentration of the gases, for example, $O_2$, $CO_2$, xenon, etc., in the inspiratory section gases and the expiratory section gases in the anesthesia delivery and ventilation system 100.

Figure 4A:
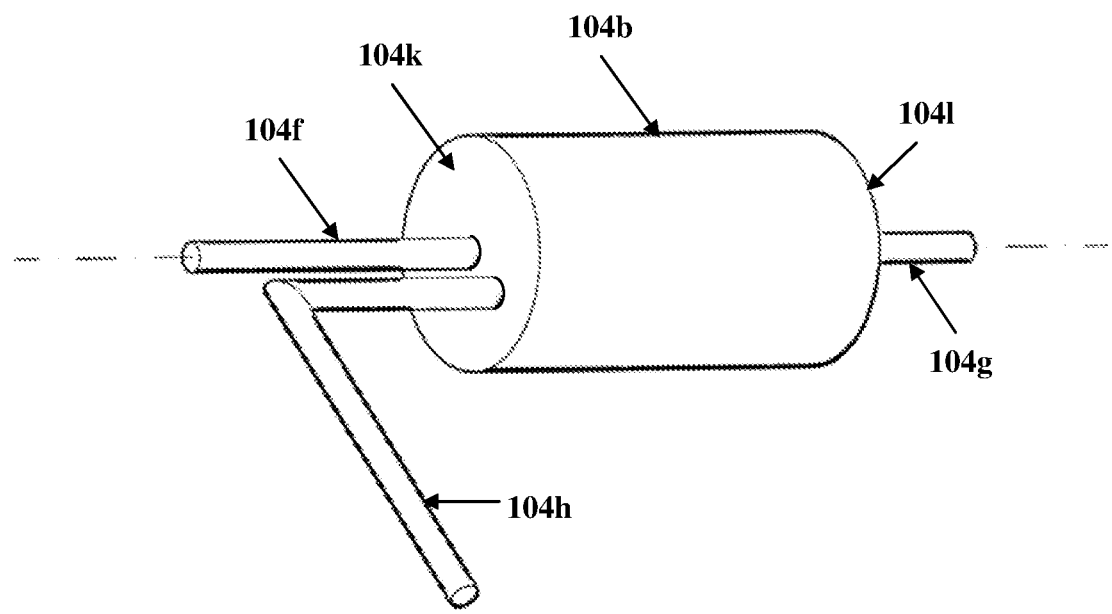
FIG. 4A exemplarily illustrates a perspective view of a ventilation drive system of the embodiment of the anesthesia delivery and ventilation system shown in FIG. 3.

FIG. 4A exemplarily illustrates a perspective view of the ventilation drive system 104 of the embodiment of the anesthesia delivery and ventilation system 100 shown in FIG. 3. The inlet ventilation tube 104f and the outlet ventilation tube 104g of the ventilation drive system 104 extend from opposing ends 104k and 104l of the ventilation housing 104b of the ventilation drive system 104. The tube 104h extends from the end 104k of the ventilation housing 104b to the ventilation blower 104a and the elastic manual ventilation bag 104j as exemplarily illustrated in FIG. 3.

Figure 4B:
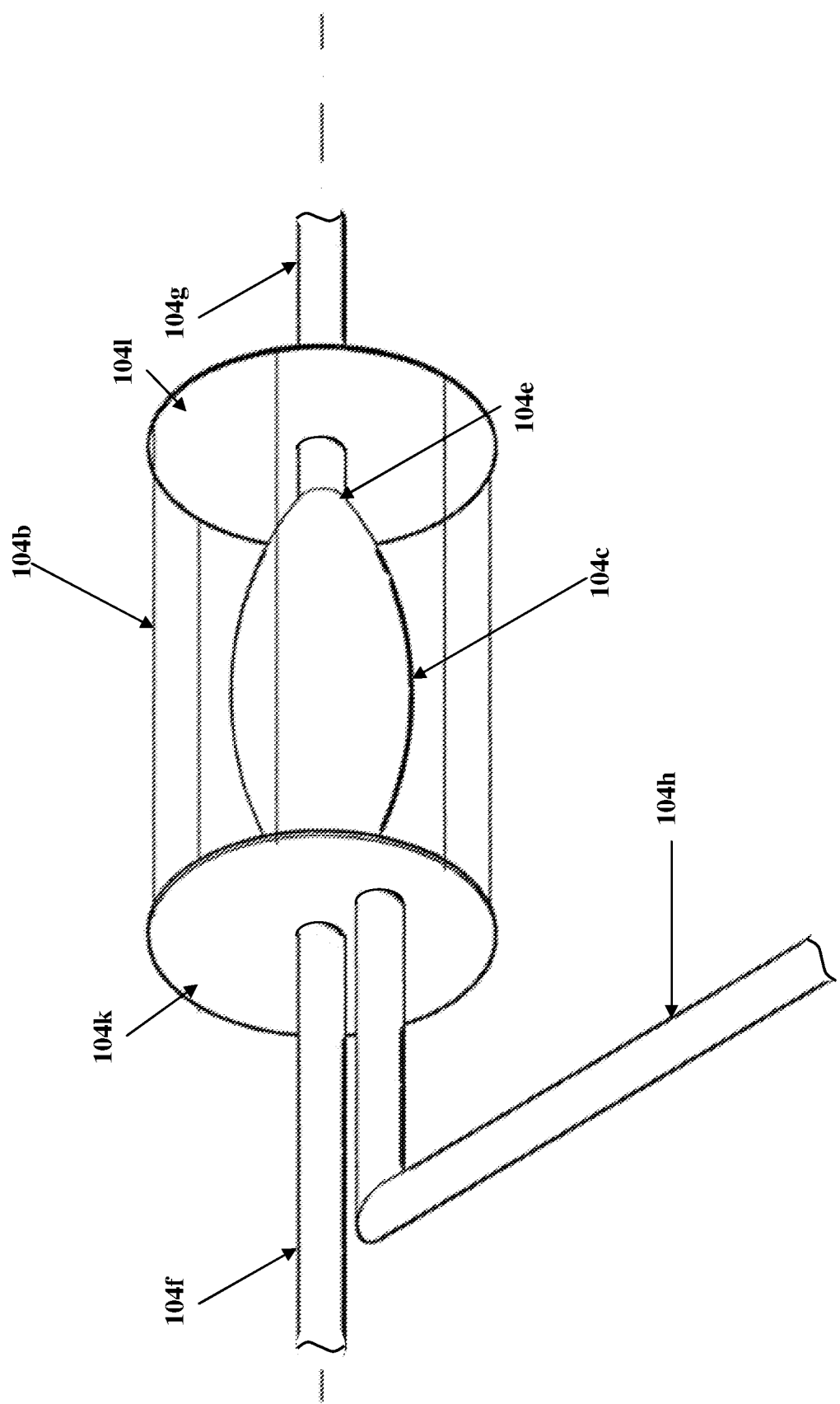
FIGS. 4B-4C exemplarily illustrate perspective internal views of the ventilation drive system of the embodiment of the anesthesia delivery and ventilation system shown in FIG. 3.
Figure 4C:
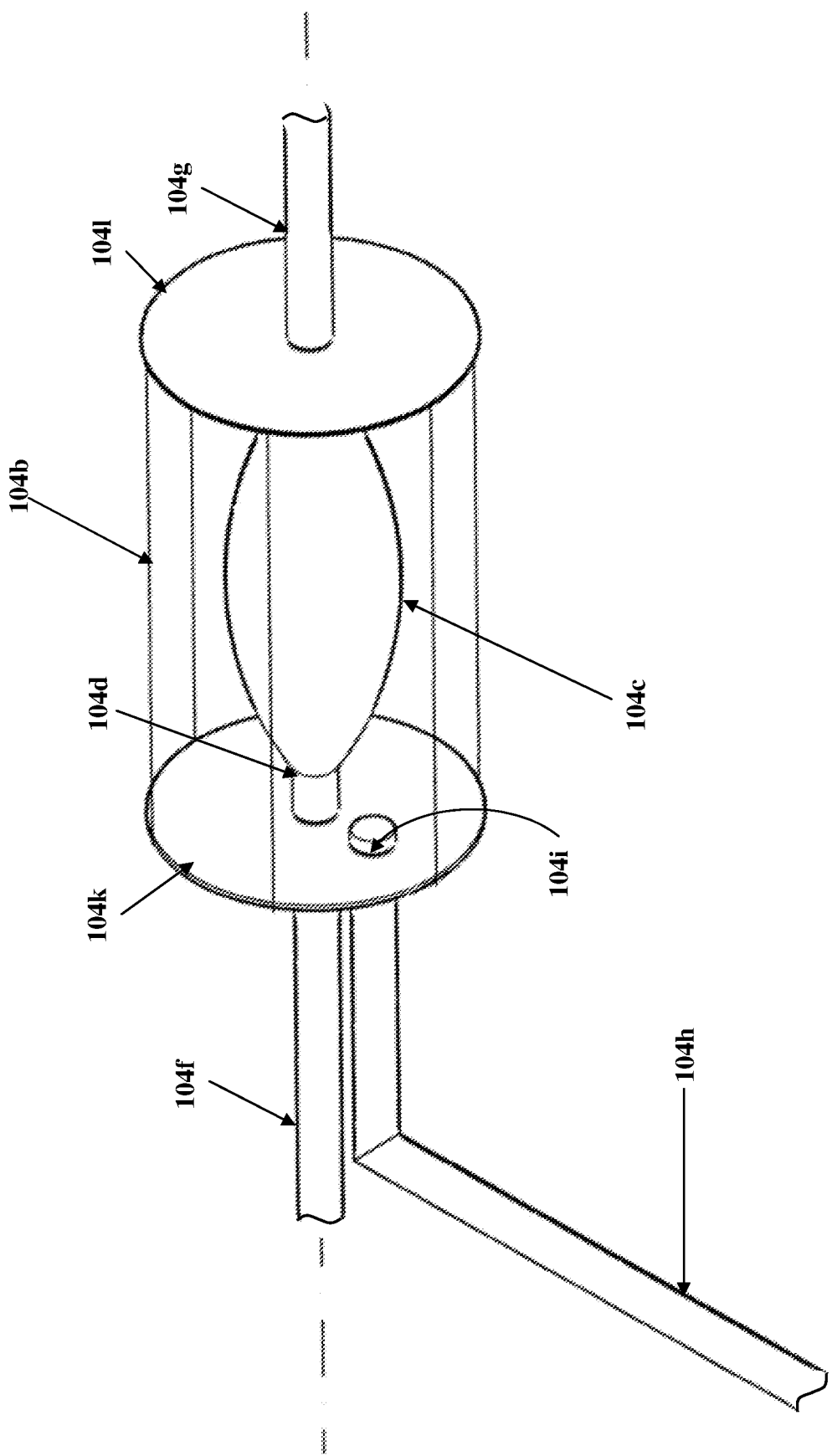

FIGS. 4B-4C exemplarily illustrate perspective internal views of the ventilation drive system 104 of the embodiment of the anesthesia delivery and ventilation system 100 shown in FIG. 3. As exemplarily illustrated in FIGS. 4B-4C, the elastic ventilation and mixing reservoir 104c is accommodated within the ventilation housing 104b between the inlet ventilation tube 104f and the outlet ventilation tube 104g of the ventilation drive system 104. The tube 104h extends from the opening 104i of the ventilation housing 104b. The inlet ventilation tube 104f and the outlet ventilation tube 104g are connected to opposing ends 104d and 104e of the elastic ventilation and mixing reservoir 104c.

Figure 4D:
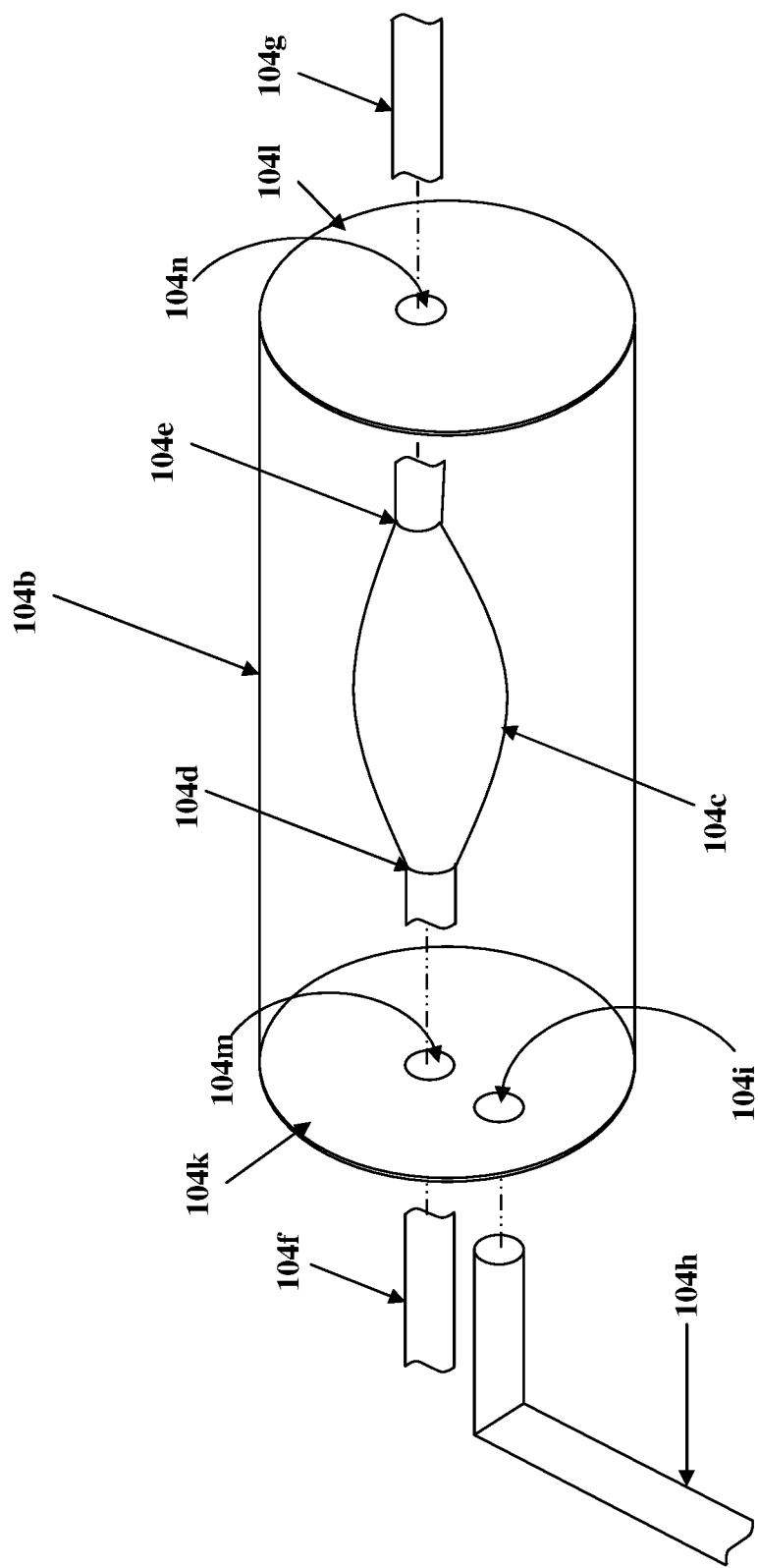
FIG. 4D exemplarily illustrates an exploded view of the ventilation drive system of the embodiment of the anesthesia delivery and ventilation system shown in FIG. 3.

FIG. 4D exemplarily illustrates an exploded view of the ventilation drive system 104 of the embodiment of the anesthesia delivery and ventilation system 100 shown in FIG. 3. The exploded view in FIG. 4D exemplarily illustrates the openings 104i, 104m, and 104n positioned on the opposing ends 104k and 104l of the ventilation housing 104b. The inlet ventilation tube 104f is inserted through the opening 104m on one end 104k of the ventilation housing 104b and connected to the end 104d of the elastic ventilation and mixing reservoir 104c. The outlet ventilation tube 104g connected to the end 104e of the elastic ventilation and mixing reservoir 104c exits through the opening 104n on the opposing end 104l of the ventilation housing 104b. The tube 104h extends from the opening 104i of the ventilation housing 104b to the ventilation blower 104a and the elastic manual ventilation bag 104j as exemplarily illustrated in FIG. 3.

Figure 5:
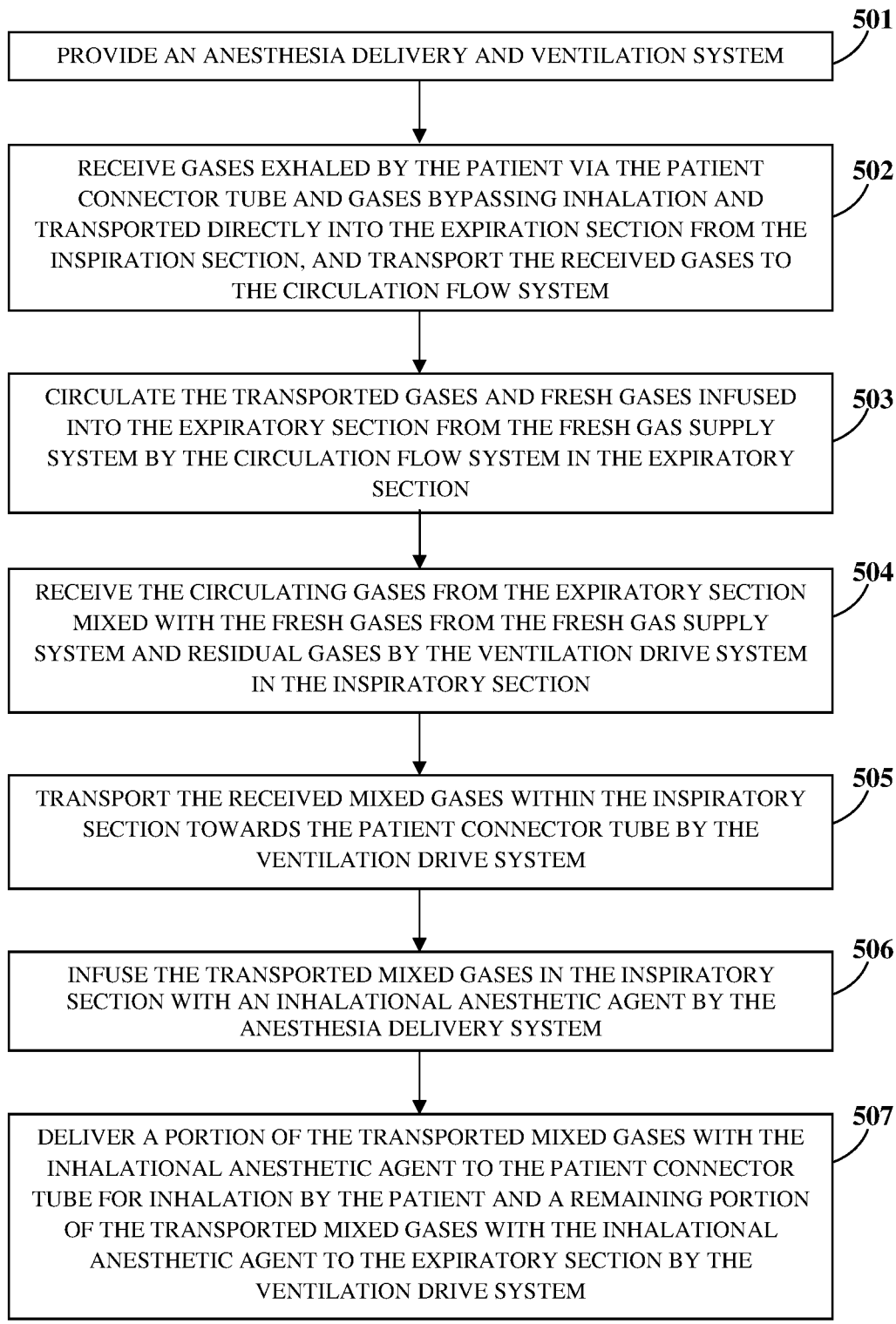
FIG. 5 illustrates a method for delivering inspiratory section gases optionally infused with an inhalational anesthetic agent to a patient and for controlling positive end-expiratory pressure and ventilation of the inspiratory section gases without the use of a proportional valve.

FIG. 5 illustrates a method for delivering inspiratory section gases optionally infused with an inhalational anesthetic agent to a patient and for controlling positive end-expiratory pressure and ventilation of the inspiratory section gases without the use of a proportional valve. In the method disclosed herein, the anesthesia delivery and ventilation system 100 comprising the expiratory section 101, the circulation flow system 102, the inspiratory section 103, the ventilation drive system 104, and the anesthesia delivery system 105 as exemplarily illustrated in FIGS. 1-4D and as disclosed in the detailed description of FIGS. 1-4D, is provided 501. The expiratory section 101 receives 502 gases exhaled by the patient via the patient connector tube 108 and gases that bypass inhalation and which are transported directly into the expiratory section 101 from the inspiratory section 103, and transports 502 the received gases to the circulation flow system 102. One or more carbon dioxide absorbers 106a and 106b positioned between the first end 101a of the expiratory section 101 and the second end 101b of the expiratory section 101 remove carbon dioxide from the expiratory section gases. The circulation flow system 102 circulates 503 the transported gases and fresh gases infused into the expiratory section 101 from the fresh gas supply system 107 to the ventilation drive system 104.

In an embodiment, the anesthesia delivery and ventilation system 100 receives the circulating gases from the circulation flow system 102 and the fresh gases from the fresh gas supply system 107 in at least one elastic mixing reservoir 109 connected to the circulation flow system 102, the fresh gas supply system 107, and the inspiratory section 103 via the connector element 110. The elastic mixing reservoir 109 mixes the received gases with residual gases contained in the elastic mixing reservoir 109. The ventilation drive system 104 receives 504 the mixed gases comprising the circulating gases from the expiratory section 101 mixed with the fresh gases from the fresh gas supply system 107 and the residual gases from the elastic mixing reservoir 109. The ventilation drive system 104 transports 505 the received mixed gases within the inspiratory section 103 towards the patient connector tube 108.

If required, the anesthesia delivery system 105 infuses 506 the transported mixed gases in the inspiratory section 103 with the inhalational anesthetic agent. The ventilation drive system 104 delivers 507 a portion of the transported mixed gases with the inhalational anesthetic agent to the patient connector tube 108 for inhalation by the patient and the remaining portion of the transported mixed gases with the inhalational anesthetic agent that bypasses the inhalation process to the expiratory section 101. The ventilation drive system 104 and the circulation flow system 102 provide flow control of the mixed gases and optionally the inhalational anesthetic agent in the inspiratory section 103 to the patient. The ventilation drive system 104 and the circulation flow system 102 are controlled by the computer system 119 independently of each other and operate independently of each other to provide positive end-expiratory pressure control and ventilation control to the patient at the patient connector tube 108 without the use of a proportional valve in the circulating loop of the anesthesia delivery and ventilation system 100.

The foregoing examples have been provided merely for the purpose of explanation and are in no way to be construed as limiting of the method and the anesthesia delivery and ventilation system 100 disclosed herein. While the method and the anesthesia delivery and ventilation system 100 have been described with reference to various embodiments, it is understood that the words, which have been used herein, are words of description and illustration, rather than words of limitation. Further, although the method and the anesthesia delivery and ventilation system 100 have been described herein with reference to particular means, materials, and embodiments, the method and the anesthesia delivery and ventilation system 100 are not intended to be limited to the particulars disclosed herein; rather, the method and the anesthesia delivery and ventilation system 100 extends to all functionally equivalent structures, methods and uses, such as are within the scope of the appended claims. Those skilled in the art, having the benefit of the teachings of this specification, may effect numerous modifications thereto and changes may be made without departing from the scope and spirit of the method and the anesthesia delivery and ventilation system 100 disclosed herein in their aspects.

We claim:

1. An anesthesia delivery and ventilation system, comprising:

an expiratory section comprising one or more carbon dioxide ($CO_2$) absorbers, a circulation flow system, and a fresh gas supply system comprising oxygen supply, air supply, and supply of other gases, wherein a first end of said expiratory section is operably connected to a patient connector tube for receiving gases exhaled by a patient via the patient connector tube and gases bypassing inhalation and transported directly into the expiratory section from an inspiratory section, wherein a second end of said expiratory section is in-line with one or more elastic mixing reservoirs, and wherein said expiratory section increases concentration of the received gases to a gas component level required to be maintained in the inspiratory section;

said circulation flow system comprising a circulation blower operably positioned at a predetermined location in the expiratory section for circulating the expiratory section gases substantially free of carbon dioxide, wherein the circulation flow system is controlled by a feedback control loop based on a set of integrated flow rate, temperature, and pressure-sensors located in the expiratory section, inspiration section and patient tube, and wherein the fresh gases from the fresh gas supply system are mixed with the circulating gases proximal to the second end of the expiratory section;

said one or more elastic mixing reservoirs in fluid communication with the circulation flow system and the fresh gas supply system via a connector element for receiving the circulating gases from the circulation flow system and the fresh gases from the fresh gas supply system, wherein said one or more elastic mixing reservoirs mix the received circulating gases and the received fresh gases with the residual gases contained in the one or more elastic mixing reservoirs;

said inspiratory section in fluid communication with the circulation flow system and the fresh gas supply system at the second end of the expiratory section via said one or more elastic mixing reservoirs, wherein the inspiratory section comprises a ventilation drive system and an anesthesia delivery system, wherein said inspiratory section comprises a first end and a second end, wherein the first end of the inspiratory section is proximal to and in fluid communication with the second end of the expiratory section via said one or more elastic mixing reservoirs, wherein the second end of the inspiratory section is operably connected to the patient connector tube, and wherein the inspiratory section is configured to receive the mixed gases from the expiratory section and residual gases within said one or more elastic mixing reservoirs;

a ventilation drive system comprising a ventilation blower operably positioned at a predetermined location in the inspiratory section for receiving the mixed gases and the residual gases from said one or more elastic mixing reservoirs and delivering the mixed gases and the residual gases infused with an inhalational anesthetic agent to the patient and for providing ventilation control to the patient when lungs of the patient are ventilated, wherein the ventilation blower provides controlled inhalation and/or exhalation ventilation patterns to the patient, wherein the ventilation drive system and the circulation flow system are configured to provide flow control of the mixed gases, the residual gases, and the inhalational anesthetic agent in the inspiratory section to the patient, and wherein the ventilation drive system and the circulation flow system are independently controlled and operate independently of each other using the integrated flow rate, temperature, and pressure sensors in the expiratory section, inspiratory section, the fresh gas supply system, and patient tube section, and wherein the ventilation drive system and the circulation flow system provide positive end-expiratory pressure control and ventilation control to the patient without use of a proportional valve in the anesthesia delivery and ventilation system; and an anesthesia delivery system operably connected to the inspiratory section and in fluid communication with the inspiratory section, wherein the anesthesia delivery system is positioned between the first end of the inspiratory section and the second end of the inspiratory section for infusing and vaporizing the inhalational anesthetic agent into the mixed gases and the residual gases in the inspiratory section, and wherein the ventilation drive system delivers a portion of the mixed gases and the residual gases with the inhalational anesthetic agent to the patient connector tube for inhalation by the patient and a remaining portion of the mixed gases and the residual gases with the inhalational anesthetic agent to the expiratory section.

2. The anesthesia delivery and ventilation system of claim 1, wherein the circulation blower circulates the gases from the patient connector tube within the expiratory section and the gases bypassing the inhalation and transported directly into the expiratory section from the inspiratory section.

3. The anesthesia delivery and ventilation system of claim 1, further comprising one or more breathing gas concentration sensors positioned at predetermined locations within the anesthesia delivery and ventilation system for measuring concentrations of the gases in the expiratory section, the mixed gases in the inspiratory section, the fresh gases, and the inhalational anesthetic agent at the predetermined locations within the anesthesia delivery and ventilation system.

4. The anesthesia delivery and ventilation system of claim 1, wherein said one or more elastic mixing reservoirs are in fluid communication with the circulation flow system and the fresh gas supply system via a connector element for receiving the circulating gases from the circulation flow system and the fresh gases from the fresh gas supply system, wherein said one or more elastic mixing reservoir mix the received circulating gases and the received fresh gases with the residual gases contained in the one or more elastic mixing reservoirs.

5. The anesthesia delivery and ventilation system of claim 4, wherein the connector element comprises:
 a stopper positioned on an upper end of the one or more elastic mixing reservoirs for containing the circulating gases, the fresh gases, and the residual gases in the one or more elastic mixing reservoirs, the stopper comprising a first opening positioned about a central axis of the stopper, and a second opening positioned transaxial to the central axis of the first opening of the stopper;
 an inlet tube inserted into the first opening of the stopper, the inlet tube in fluid communication with the expiratory section and operably connected to the second end of the expiratory section for transporting the circulating gases from the circulation flow system and the fresh gases from the fresh gas supply system to the one or more elastic mixing reservoirs; and
 an outlet tube inserted into the second opening of the stopper and positioned substantially perpendicular to the inlet tube, the outlet tube in fluid communication with the one or more elastic mixing reservoirs and operably connected to the first end of the inspiratory section for receiving the mixed gases and the residual gases from the one or more elastic mixing reservoirs and transporting the mixed gases and the residual gases to the inspiratory section.

6. A method for delivering gases optionally infused with an inhalational anesthetic agent to a patient and controlling positive end-expiratory pressure and ventilation patterns to the patient without use of a proportional valve, the method comprising:
 providing the anesthesia delivery and ventilation system of claim 1;
 receiving gases exhaled by the patient via the patient connector tube and gases bypassing inhalation and transported directly into the expiratory section from the inspiratory section, and transporting the received gases to the circulation flow system;
 circulating the transported gases and fresh gases infused into the expiratory section from the fresh gas supply system, by the circulation flow system in the expiratory section;
 receiving the circulating gases from the expiratory section mixed with the fresh gases from the fresh gas supply system by the ventilation drive system in the inspiratory section;
 transporting the received mixed gases within the inspiratory section towards the patient connector tube by the ventilation drive system, wherein the ventilation drive system and the circulation flow system are configured to provide flow control of the mixed gases and optionally the inhalational anesthetic agent in the inspiratory section to the patient, and wherein the ventilation drive system and the circulation flow system are controlled and operate independently of each other to provide positive end-expiratory pressure control and ventilation control to the patient without use of a proportional valve in the anesthesia delivery and ventilation system;
 infusing the transported mixed gases in the inspiratory section with the inhalational anesthetic agent by the anesthesia delivery system; and
 delivering a portion of the transported mixed gases with the inhalational anesthetic agent to the patient connector tube for inhalation by the patient and a remaining portion of the transported mixed gases with the inhalational anesthetic agent to the expiratory section by the ventilation drive system.

7. The method of claim 6, further comprising receiving and mixing the circulating gases from the circulation flow system and the fresh gases from the fresh gas supply system with residual gases contained in one elastic mixing reservoir operably connected to and in fluid communication with the circulation flow system, the fresh gas supply system, and the inspiratory section via a connector element.

8. The method of claim 6, further comprising measuring flow rate, temperature, and pressure of the fresh gases, the gases in the expiratory section, and the mixed gases in the inspiratory section at the predetermined locations within the anesthesia delivery and ventilation system using the flow rate, temperature and pressure sensors positioned at the predetermined locations within the anesthesia delivery and ventilation system.

9. The method of claim 6, further comprising measuring concentrations of the gases in the expiratory section, the mixed gases in the inspiratory section, the fresh gases, and the inhalational anesthetic agent at predetermined locations within the anesthesia delivery and ventilation system by one or more breathing gas concentration sensors positioned at the predetermined locations within the anesthesia delivery and ventilation system.

10. An anesthesia delivery and ventilation system comprising:
an expiratory section comprising one or more carbon dioxide ($CO_2$) absorbers, a circulation flow system, and a fresh gas supply system comprising oxygen supply, air supply, and supply of other gases, wherein a first end of said expiratory section is operably connected to a patient connector tube for receiving gases exhaled by a patient via the patient connector tube and gases bypassing inhalation and transported directly into the expiratory section from an inspiratory section, wherein a second end of said expiratory section is in-line with a to ventilation drive system, and wherein said expiratory section increases concentration of the received gases to a gas component level required to be maintained in the inspiratory section;
said circulation flow system comprising a circulation blower operably positioned at a predetermined location in the expiratory section for circulating the expiratory section gases substantially free of carbon dioxide, wherein the circulation flow system is controlled by a feedback control loop based on a set of integrated flow rate, temperature, and pressure-sensors located in the expiratory section, inspiration section and patient tube, and wherein the fresh gases from the fresh gas supply system are mixed with the circulating gases proximal to the second end of the expiratory section;
said inspiratory section in fluid communication with said expiratory section, wherein the inspiratory section comprises a ventilation drive system and an anesthesia delivery system, wherein a first end of the inspiratory section is in fluid communication with the expiratory section and a second end is in fluid communication with the patient connector tube;
said ventilation drive system comprising:
a ventilation housing;
an elastic ventilation and mixing reservoir accommodated within the ventilation housing, the elastic ventilation and mixing reservoir configured to receive the mixed gases from the expiratory section;
an inlet ventilation tube and an outlet ventilation tube connected to opposing ends of the elastic ventilation and mixing reservoir within the ventilation housing, wherein the inlet ventilation tube is inserted through a first opening of the ventilation housing and is in fluid communication with the circulation flow system and the fresh gas supply system via the second end of the expiratory section for receiving the circulating gases from the expiratory section mixed with the fresh gases from the fresh gas supply system and transporting the mixed gases to the elastic ventilation and mixing reservoir, and wherein the outlet ventilation tube is inserted through a second opening of the ventilation housing and is in fluid communication with the inspiratory section for transporting the mixed gases from the elastic ventilation and mixing reservoir to the second end of the inspiratory section;
a ventilation blower operably connected to the ventilation housing and isolated from the elastic ventilation and mixing reservoir for transporting the mixed gases received in the elastic ventilation and mixing reservoir through the inspiratory section; and
an elastic manual ventilation bag in fluid communication with the ventilation blower and operably connected to the ventilation housing for transporting the mixed gases received in the elastic ventilation and mixing reservoir through the inspiratory section, wherein the elastic manual ventilation bag is isolated from the elastic ventilation and mixing reservoir; and
an anesthesia delivery system operably connected to the inspiratory section and in fluid communication with the inspiratory section, wherein the anesthesia delivery system is positioned between the first end of the inspiratory section and the second end of the inspiratory section for infusing and vaporizing the inhalational anesthetic agent into the mixed gases in the inspiratory section, and wherein the ventilation drive system delivers a portion of the mixed gases with the inhalational anesthetic agent to the patient connector tube for inhalation by the patient and a remaining portion of the mixed with the inhalational anesthetic agent to the expiratory section.

11. The anesthesia delivery and ventilation system of claim 10, wherein the circulation blower circulates the gases from the patient connector tube within the expiratory section and the gases bypassing the inhalation and transported directly into the expiratory section from the inspiratory section.

12. The anesthesia delivery and ventilation system of claim 10, further comprising one or more breathing gas concentration sensors positioned at predetermined locations within the anesthesia delivery and ventilation system for measuring concentrations of the gases in the expiratory section, the mixed gases in the inspiratory section, the fresh gases, and the inhalational anesthetic agent at the predetermined locations within the anesthesia delivery and ventilation system.

* * * * *